(12) United States Patent
Weston et al.

(10) Patent No.: US 6,391,593 B1
(45) Date of Patent: May 21, 2002

(54) MODIFIED NUCLEIC ACID PROBES AND USE THEREOF

(75) Inventors: Anthony Weston, Northolt; Rene Assenberg, Banbury; Peter Marsh, Leamington Spa; Graham A Mock, Thame; Trevor D Ray, Abingdon; Susan D Wharam, Coventry; Donald L. N. Cardy, Aston Le Walls, all of (GB)

(73) Assignee: Cytocell Limited, Banbury (GB)

( * ) Notice: Subject to any disclaimer, the term of this patent is extended or adjusted under 35 U.S.C. 154(b) by 0 days.

(21) Appl. No.: 09/308,759
(22) PCT Filed: Jan. 26, 1999
(86) PCT No.: PCT/GB99/00265
§ 371 Date: Jul. 19, 1999
§ 102(e) Date: Jul. 19, 1999
(87) PCT Pub. No.: WO99/37806
PCT Pub. Date: Jul. 29, 1999

(30) Foreign Application Priority Data

Jan. 27, 1998 (GB) ............................... 9801628
Apr. 29, 1998 (GB) ............................... 9809014

(51) Int. Cl.[7] ............... C12P 19/34; C12Q 1/68; G01N 33/00; C07H 21/02; C07H 21/04
(52) U.S. Cl. .......... 435/91.2; 435/6; 435/91.1; 436/94; 536/23.1; 536/24.3; 536/24.33
(58) Field of Search ............ 435/6, 91.1, 91.2, 435/91.3, 91.31, 91.5, 91.51, 183; 436/94, 501; 536/23.1, 24.3, 24.33, 25.3

(56) References Cited

U.S. PATENT DOCUMENTS 5,451,503 A * 9/1995 Hogan et al. .................. 435/6
5,674,683 A * 10/1997 Kool .............................. 435/6

(List continued on next page.)

FOREIGN PATENT DOCUMENTS

EP 361983 B1 5/1996
EP 0552931 B1 5/2000

(List continued on next page.)

OTHER PUBLICATIONS

Tyagi et al., Molecular beacons: probes that fluoresce upon hybridization. Nature Biotechnology, 14, 303–308, Mar. 1996.*

(List continued on next page.)

Primary Examiner—Ethan C. Whisenant
Assistant Examiner—Frank Lu
(74) Attorney, Agent, or Firm—Pillsbury Winthrop LLP

(57) ABSTRACT

Disclosed is a method of detecting a nucleic acid sequence of interest in a sample, the method comprising contacting the sample with first and second probes; the first probe comprising a portion complementary to the sequence of interest and so capable of hybridising thereto, and a portion non-complementary to the sequence of interest; the second probe comprising a portion complementary to the sequence of interest and so capable of hybridising thereto, and a portion non-complementary to the sequence of interest but complementary to that portion of the first probe which is non-complementary to the sequence of interest, such that the first and second probes are capable of hybridising to the sequence of interest in an adjacent or substantially adjacent manner, so as to allow complementary portions of the first and second probes to hybridize to each other; causing extension of the first probe with a nucleic acid polymerase, using the second probe as a template; and detecting directly or indirectly the extension of the first probe, so as to indicate the presence of the sequence of interest; characterised in that the first and/or second probe comprises a destabilizing moiety which cannot base pair with the reciprocal probe, thereby preventing hybridisation of the first and second probes in the absence of the sequence of interest.

21 Claims, 15 Drawing Sheets

U.S. PATENT DOCUMENTS 5,843,650 A * 12/1998 Segev .......................... 435/6
6,096,880 A *  9/2000 Kool ......................... 536/25.3

FOREIGN PATENT DOCUMENTS

| WO | WO 93/06240 | 4/1993 |
| WO | WO 93/22461 | 11/1993 |
| WO | WO 9403637 | 2/1994 |
| WO | WO 9429485 | 12/1994 |
| WO | WO 9623903 | 8/1996 |

OTHER PUBLICATIONS

Tyagi S. et al., Molecular Beacons: Probes That Fluoresce Upon Hybridization Bio/Technology, Mar. 1, 1996.

* cited by examiner

FIG. 11D  FIG. 11C

FIG. 13A
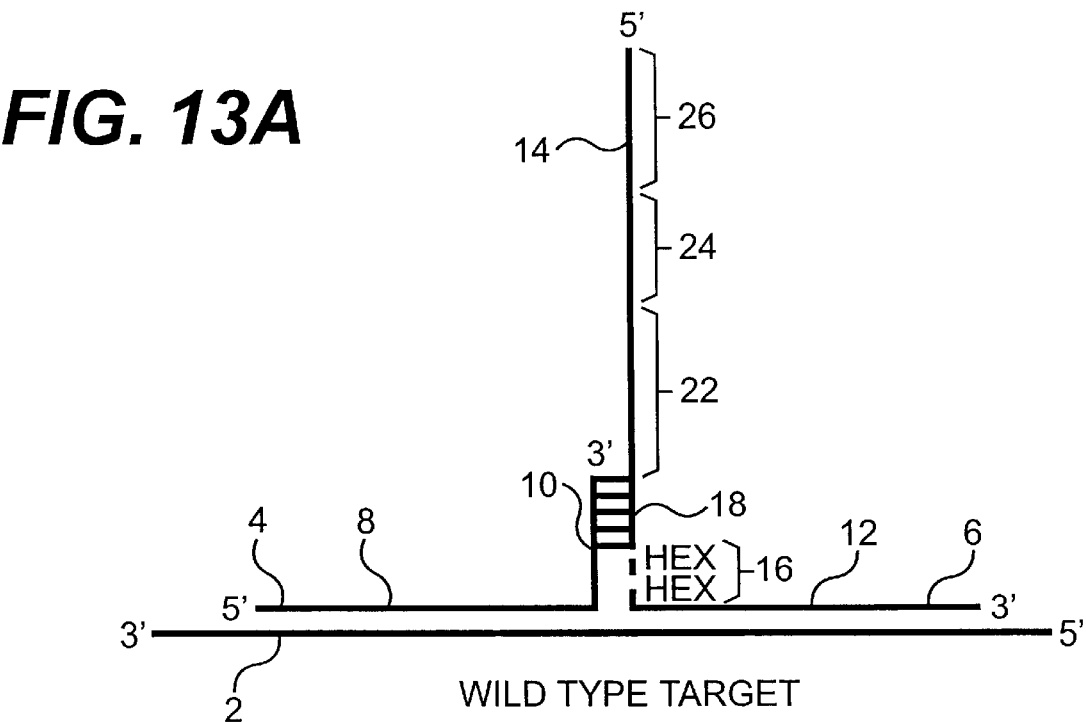
WILD TYPE TARGET
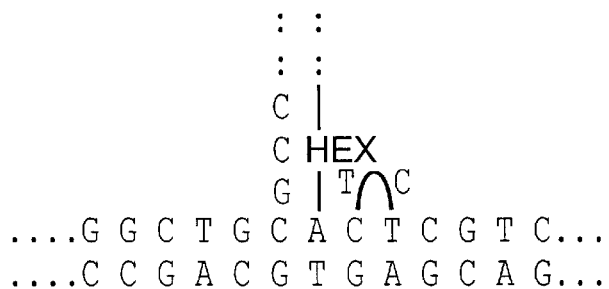
FIG. 13B
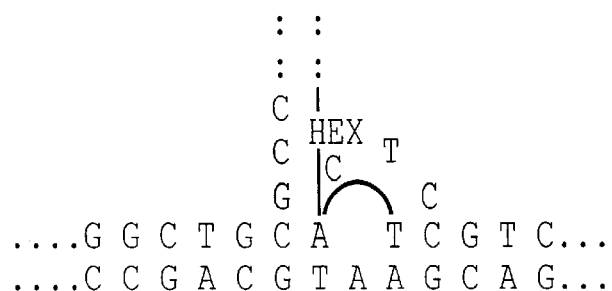
FIG. 13C

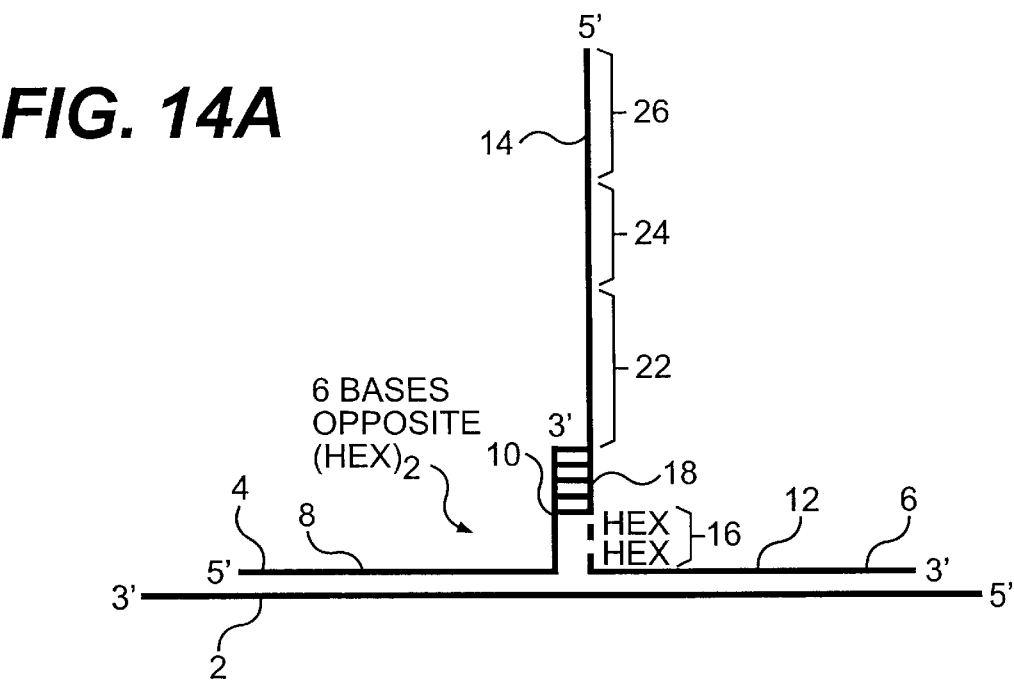
FIG. 14A
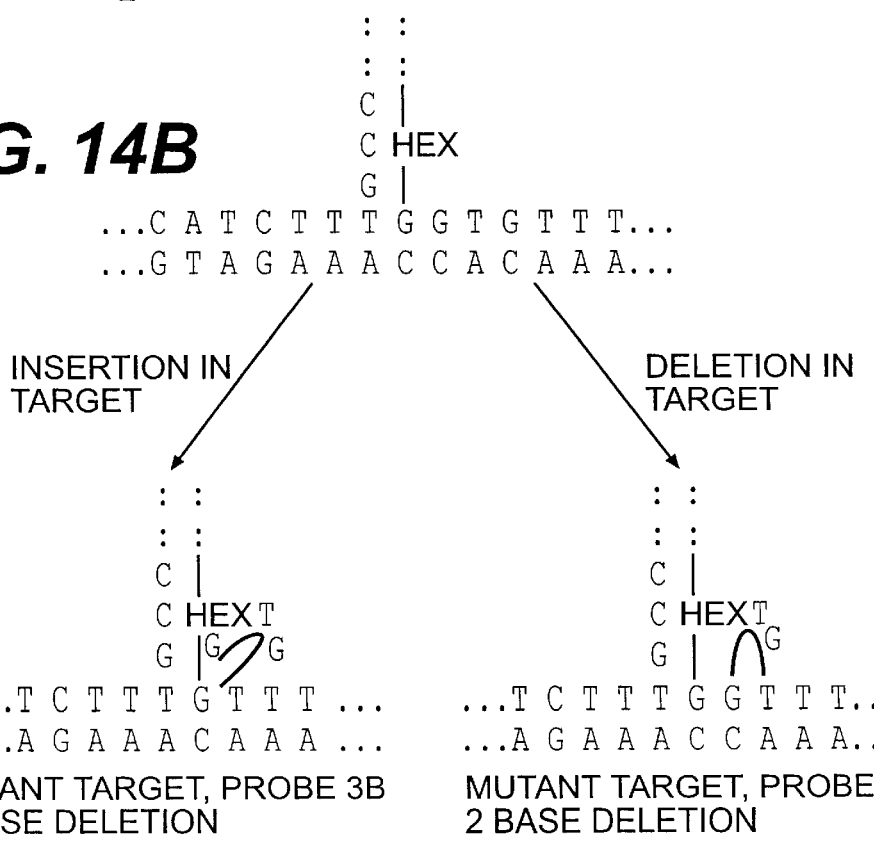
FIG. 14B
MUTANT TARGET, PROBE 3B
3 BASE DELETION
FIG. 14D
MUTANT TARGET, PROBE 3C
2 BASE DELETION
FIG. 14C

MODIFIED NUCLEIC ACID PROBES AND USE THEREOF

FIELD OF THE INVENTION

The present invention relates to the introduction of destabilizing moieties into oligonucleotide probes for the improvement of nucleic acid amplification processes, methods comprising the use of such oligonucleotide and to kits for performing nucleic acid amplification processes comprising such oligonucleotide probes. The present invention is particularly concerned with amplification of hybridised modified nucleic acid probes such that sensitivity and specificity of the reaction is increased.

BACKGROUND OF THE INVENTION

All publications mentioned in the present specification are herein incorporated by reference.

A number of nucleic acid amplification processes are cited in the literature and disclosed in published European and PCT patent applications. One such process known as polymerase chain reaction (PCR) is disclosed in U.S. Pat. Nos. 4,683,195 and 4,683,202. The PCR process consists of nucleic acid primers that anneal to opposite strands of a DNA duplex; these primers are extended using thermostable DNA polymerase in the presence of nucleotide triphosphates to yield two duplex copies of the original nucleic acid sequence. Successive cycles of denaturation, annealing and extension are undertaken to further amplify copies of the original nucleic acid sequence. This method has its drawbacks including the need for adjusting reaction temperatures alternately between intermediate (e.g. 50° C.–55° C.) and high (e.g. 90° C.–95° C.) temperatures involving repeated thermal cycling. Also the time scale required for multiple cycles of large temperature transitions to achieve amplification of a nucleic acid sequence and the occurrence of sequence errors in the amplified copies of the nucleic acid sequence is a major disadvantage as errors occur during multiple copying of long sequence tracts. Additionally, detection of the amplified nucleic acid sequence generally requires further processes e.g. agarose gel electrophoresis.

Alternative nucleic acid amplification processes are disclosed WO 88/10315 (Siska Diagnostics). EP 329,822 (Cangene) and 373,960 (Siska Diagnostics). U.S. Pat. No. 5,554,516 (Gen-Probe Inc.), and WO 89/1050 & 88/10315 assigned to Burg et al. and Gingeras et al., respectively. These amplification processes describe a cycling reaction comprising of alternate DNA and RNA synthesis. This alternate RNA/DNA synthesis is achieved principally through the annealing of oligonucleotides adjacent to a specific DNA sequence whereby these oligonucleotides comprise a transcriptional promoter. The RNA copies of the specific sequence so produced, or alternatively an input sample comprising a specific RNA sequence (U.S. Pat. No. 5,554,516), are then copied as DNA strands using a nucleic acid primer and the RNA from the resulting DNA:RNA hybrid is either removed by denaturation (WO 88/10315) or removed with RNase H (EP 329822, EP 373960 & U.S. Pat. No. 5,554,516). The annealing of oligonucleotides forming a transcription promoter is then repeated in order to repeat RNA production.

Amplification is thus achieved principally through the use of efficient RNA polymerases to produce an excess of RNA copies over DNA templates. The RNase version of this method has great advantages over PCR in that amplification can potentially be achieved at a single temperature (i.e. isothermally). Additionally, a much greater level of amplification can be achieved than for PCR i.e. a doubling of DNA copies per cycle for PCR, compared to 10–100 RNA copies using T7 RNA polymerase. A disadvantage associated with the DNA:RNA cycling method described in EP 329822 is that it requires test nucleic acid with discrete ends for the annealing of oligonucleotides to create the transcriptional promoter. This poses difficulties in detection of, for example, specific genes in long DNA molecules. Further disadvantages of this method are that at least three enzymes are required to undertake the DNA:RNA cycling with potentially deleterious consequences for stability, cost and reproducibility; and that one or more further processes are often required (e.g. gel electrophoresis) for detection of the amplified nucleic acid sequence.

The processes described above all refer to methods whereby a specific nucleic acid region is directly copied and these nucleic acid copies are further copied to achieve amplification. The variability between various nucleic acid sequences is such that the rates of amplification between different sequences by the same process are likely to differ thus presenting problems for example in the quantitation of the original amount of specific nucleic acid.

The processes listed above have a number of disadvantages in the amplification of their target nucleic acid; therefore, a list of desiderata for the sensitive detection of a specific target nucleic acid sequence is outlined below:

a) the process should preferably not require copying of the target sequence;

b) the process should preferably not involve multiple copying of long tracts of sequence;

c) the process should preferably be generally applicable to both DNA and RNA target sequences including specific sequences without discrete ends;

d) the signal should preferably result from the independent hybridisation of two different probes; or regions of probe, to a target sequence; and e) the process should include an option for detection of hybridised probe without any additional processes.

A nucleic acid amplification process that fulfils the above desiderata is disclosed in WO 93/06240 (Cytocell Ltd). Two amplification processes are described, one thermal and one isothermal. Both the thermal and isothermal versions depend on the hybridisation of two nucleic acid probes of which regions are complementary to the target nucleic acid. Portions of said probes are capable of hybridising to the sequence of interest such that the probes are adjacent or substantially adjacent to one another, so as to enable complementary "arm" specific sequences of the first and second probes to become annealed to each other. Following annealing, chain extension of one of the probes is achieved by using part of the other probe as a template.

Amplification is achieved by one of two means; in the thermal cycling version thermal separation of the extended first probe is carried out to allow hybridisation of a further probe, substantially complementary to part of the newly synthesised sequence of the extended first probe. Extension of the further probe by use of an appropriate polymerase using the extended first probe as a template is achieved. Thermal separation of the extended first and further probe products allows these molecules to act as a template for the extension of further first probe molecules and the extended first probe can act as a template for the extension of other further probe molecules. In the isothermal version, primer extension of the first probe creates a functional RNA polymerase promoter that in the presence of a relevant RNA polymerase transcribes multiple copies of RNA. The resulting RNA is further amplified as a result of the interaction of complementary DNA oligonucleotides containing further RNA polymerase promoter sequences, whereupon annealing of the RNA on the DNA oligonucleotide and a subsequent extension reaction leads to a further round of RNA synthesis. This cyclical process generates large yields of RNA, detection of which can be achieved by a number of means. The present invention is related to these processes and aims to provide improvements thereon.

SUMMARY OF THE INVENTION

In preferred embodiments the present invention also fulfils all the aforementioned desiderata. This may be achieved through the hybridisation of two oligonucleotide probes that contain complementary target specific regions together with complementary arm regions, such that in the presence of the target sequence of interest the target and the two probes form a "three way junction". Within the complementary arm region of one or both of the oligonucleotide probes is incorporated a destabilizing moiety that prevents the two oligonucleotide probes from associating in the absence of target nucleic acid and hence reducing noise from the potential association of these probes.

In a first aspect the invention provides a pair of nucleic acid probes for use in a method of detecting a nucleic acid target sequence of interest, a first probe comprising a portion complementary to the sequence of interest and so capable of hybridising thereto and a portion non-complementary to the sequence of interest, and a second probe comprising a portion complementary to the sequence of interest and so capable of hybridising thereto and a portion non-complementary to the sequence of interest but complementary to that portion of the first probe which is non-complementary to the sequence of interest, such that the first and second probes are capable of hybridising to the sequence of interest in an adjacent or substantially adjacent manner so as to allow complementary portions of the first and second probes to hybridise to each other, characterised in that the first and/or second probe comprises a destabilizing, moiety which cannot base pair with the reciprocal member of the pair of probes, thereby preventing hybridisation of the first and second probes in the absence of the sequence of interest.

The target strand may comprise any nucleic acid (RNA or, more preferably DNA) sequence of interest, such as a sequence from a pathogen (such that the complex may be used to detect the presence of a pathogen), or may be the sequence of a particular human, animal or plant allele, such that the genotype of an individual human or animal may be determined. Conveniently (but not necessarily) at least that portion (typically 2–4 bases) of the target which contains the part of the second strand of the double stranded promoter will preferably comprise DNA. The target strand may comprise both DNA and/or RNA.

The hybridisation of the first and second probes to each other and to the sequence of interest forms a structure which the present inventors describe as a "three way junction". The first and second probes preferably comprise DNA, PNA (peptide nucleic acid) or LNA ("locked nucleic acid"), but may comprise RNA, or any combination of the foregoing.

PNA is a synthetic nucleic acid analogue in which the sugar/phosphate backbone is replaced by a peptide-linked chain (typically of repeated N-(2-aminoethyl)-glycine units), to which the bases are joined by methylene carbonyl linkages. PNA/DNA hybrids have high Tm values compared to double stranded DNA molecules since in DNA the highly negatively-charged phosphate backbone causes electrostatic repulsion between the respective strands, whilst the backbone of PNA is uncharged. Another characteristic of PNA is that a single base mis-match is, relatively speaking, more destabilizing than a single base mis-match in heteroduplex DNA. Accordingly, PNA may advantageously be included in probes for use in the present invention, as the resulting probes have greater specificity than probes consisting entirely of DNA. Synthesis and uses of PNA have been disclosed by, for example, Orum et al, (1993 Nucl. Acids Res. 21, 5332); Egholm et al, (1992 J. Am. Chem. Soc. 114, 1895); and Egholm et al (1993 Nature 365, 566).

LNA is a synthetic nucleic acid analogue, incorporating "internally bridged" nucleoside analogues. Synthesis of LNA, and properties thereof, have been described by a number of authors: Nielsen et al, (1997 J. Chem. Soc. Perkin Trans. 1, 3423); Koshkin et al, (1998 Tetrahedron Letters 39, 4381); Singh & Wengel (1998 Chem. Commun. 1247); and Singh et al, (1998 Chem. Commun. 455). As with PNA, LNA exhibits greater thermal stability when paired with DNA, than do conventional DNA/DNA heteroduplexes. However, LNA can be synthesised on conventional nucleic acid synthesising machines, whereas PNA cannot; special linkers are required to join PNA to DNA, when forming a single stranded PNA/DNA chimera. In contrast, LNA can simply be joined to DNA molecules by conventional techniques. Therefore, in some respects, LNA is to be preferred over PNA, for use in probes in accordance with the present invention.

In particular, the target specific regions of the two probes may comprise LNA and/or PNA and the arm regions comprise DNA, with one or both of the probes comprising a destabilizing moiety. Chimeric probe molecules comprising PNA are useful only in those embodiments which do not require the copying of the PNA portions of a chimeric template, as PNA is not recognised as a template by any known nucleic acid polymerases.

It is an essential feature of the invention that the first and second probes, when hybridised to the target sequence, are adjacent or substantially adjacent to each other. Use of the term "adjacent" is herein intended to mean that there are no nucleotides of the target sequence left without base-pairing between those portions of the target sequence which are base-paired to the complementary sequence of the probes. This proximity between the probes enables the target-non-complementary sequences of the probes to anneal. As will readily be apparent to those skilled in the art, by designing the probes so as to allow for annealing to each other at greater separations from the target sequence, gaps may be introduced between the loci in the target nucleotide sequence to which the probes hybridise. In this situation the probes are said to be "substantially adjacent", because there may be some nucleotides of the target sequence left without base-pairing between those portions of the target sequence which are base-paired to the probes. Clearly, the number of intervening un-paired nucleotides of the target sequence can vary according to the design of the probes. Thus whilst it is preferred that the first and second probes hybridise so as to be adjacent, the probes may be separated by up to 5 nucleotides of target sequence, and the term "substantially adjacent" is intended to refer to such situations.

In a second aspect the invention provides a method of detecting a nucleic acid target sequence of interest, the method comprising: hybridising a pair of probes in accordance with the first aspect defined above to the sequence of interest and to each other; causing extension of one of the probes using the other probe as template (e.g. as described in WO 93/06240 or U.S. Pat. No. 5,545,516 the contents of which are herein incorporated by reference), so as to form newly-synthesised nucleic acid; and detecting directly or indirectly the newly-synthesised nucleic acid. It is strongly preferred that the first probe is extended, using the second probe as a template, so as to form an active nucleic acid promoter, such that amplification can take place, e.g. by production of a large number of RNA copies of the second probe. Typically one or more further nucleic acid probes are introduced, in the presence of appropriate polymerases, so as to facilitate amplification. In preferred embodiments, a cycling amplification is established, which leads to multiple amplifications. Details of how such amplification may be obtained are driven in the examples below and in WO 93/06240.

Desirably the newly-synthesised nucleic acid, together with the template portion of the second probe will form an RNA polymerase promoter recognised, for example, by T3, T7 or SP6 RNA polymerases, or by any of the mutant forms thereof which are known to those skilled in the art. Particular mutant RNA polymerases are known, which may be useful in performing the method of the invention, which may synthesise RNA or DNA (see Kostyuk et al, 1995 FEBS Letts. 369, 165–168).

Thus, in preferred embodiments the arm region of the second probe (with or without destabilizing moiety) comprises a sequence complementary to the arm region of the first probe (+ or − destabilizing moiety), and a unique sequence of choice such as, but not limited to, an RNA polymerase promoter sequence, a "+12 region" to enhance efficiency of transcription, followed by probe detection and capture sequences.

By way of explanation, the present inventors have found that the efficiency of initiation of RNA synthesis by the RNA polymerase promoter is affected by sequences adjacent to the promoter, downstream. In particular, a region of twelve bases (the "+12 region") is required for optimum RNA transcription. It is therefore preferred that the template portion of the second probe, which is transcribed, comprises a +12 region appropriate to the polymerase which recognises the promoter. The inventors have elucidated the optimum sequence of +12 regions for the T7 polymerase (discussed in greater detail below)—it is not known at present if these are also optimum for say, T3 and SP6 polymerases. If, as is possible, SP6 and T3 polymerases have different optimum +12 regions, it would be a simple matter for the person skilled in the art to identify the relevant sequence by trial-and-error, with the benefit of the present disclosure.

The sequences of preferred +12 regions, for inclusion in the template portion of the promoter strand, (in respect of T7 polymerase) are shown below in Table 1. The most active +12 region (giving greatest transcription) is at the top, with the other sequences shown in decreasing order of preference.

Table 1 Alternative template +1 to +12 sequences for T7 polymerase, in descending order of transcription efficiency (Seq. ID Nos. 1–10 respectively)

5' ATCGTCAGTCCC 3'
5' GCTCTCTCTCCC 3'
5' ATCCTCTCTCCC 3'
5' GTTCTCTCTCCC 3'
5' GATGTGTCTCCC 3'
5' GTTGTGTCTCCC 3'
5' ATCCTCGTGCCC 3'
5' GCTCTCGTGCCC 3'
5' GTTCTCGTGCCC 3'
5' GTTGTGGTGCCC 3'

(The 5' base is numbered as +1, being the first base downstream from the end of the promoter sequence, the 3' base as +12).

In a further embodiment, the template portion of the complex (preferably on the promoter strand) could contain sequences that can be used to identify, detect or amplify the de novo synthesised RNA copies (see, for example, WO 93/06240. U.S. Pat. No. 5,554,516, or, for example, using molecular beacon sequences such as those disclosed by Tyagi & Kramer 1996 Nature Biotech 14, 303–308). These sequences are conveniently placed adjacent to, and downstream of, a +12 region (as described above) and may comprise, but are not limited to, one or more of the following: unique "molecular beacon" sequences; capture sequences; detection probe complementary sequences: alternative RNA promoter sequences for use in an isothermal amplification cycling reaction (see below). A particular unique sequence especially useful in the present invention is provided by bases 791–820 of 16S ribosomal RNA from *Streptomyces brasiliensis* (Stackebrandt et al. 1991 Appl. Environ. Microbiol. 57, 1468–1477), which sequence has no alignment with any known human DNA or DNA of a known human pathogen.

In those embodiments where the invention involves the use of a mixture comprising both ribonucleotide triphosphates (for synthesis of RNA by an RNA polymerase) and dNTPs (for synthesis of DNA by a DNA polymerase) (e.g. where primer extension is followed by isothermal amplification), the concentration of dNTPs in the mixture will preferably not exceed 50 µM, (preferably not exceed 10 µm), as excessive concentrations of dNTPs have been found by the inventors to decrease the amount of RNA synthesised by the RNA polymerase.

In a particular embodiment, the invention provides a method of distinguishing between the presence of a sequence of interest and the presence of a closely-related variant thereof, which could differ from the sequence of interest by as little as one base (e.g. a point mutation). By selection of appropriate probe sequences, performance of the method of the invention can be made to produce very different results depending on whether the sequence present in the sample is the sequence of interest or a variant thereof. In particular, the presence of unpaired bases between the first probe and the target and/or between the second probe and the target, has been found to have a surprising effect on the amount of nucleic acid synthesised from the active promoter.

Generally, the inventors have found that design of the first probe to introduce a small number (e.g. 1–3) of bases unpaired with the sequence of interest, tends to reduce the amount of nucleic acid synthesised from the promoter. Conversely, and wholly unexpectedly, the inventors have found that the presence in the second probe of a small number (e.g. 1–3) of bases unpaired with the sequence of interest can decrease or increase the amount of nucleic acid synthesised from the promoter (the unpaired bases being near the "arm" portion of the probe, such that the unpaired bases may be seen in some embodiments as a continuation of the target non complementary arm). The equivalent situation exists where there may be bases in the target sequence which are unpaired with the first probe (tending to cause a reduction in nucleic acid synthesis) or unpaired with the second probe (tending to have the opposite effect). In some embodiments, both the target and one or both probes may contain unpaired bases.

Without wishing to be bound by any particular theory, one hypothesis of the inventors is that the presence of unpaired bases between the second probe (which normally will also comprise the destabilizing moiety) and the target may, in some circumstances increase the flexibility of the resulting complex, thereby improving the access of bulky polymerase molecules to the promoter, and consequently increasing signal. In other circumstances the presence of unpaired bases can destabilize the interaction between the first and/or second probe and the target, thereby decreasing the amount of signal.

Thus, the inventors believe that inclusion of mismatches between the second probe and the sequence of interest should preferably be adjacent or substantially adjacent to the destabilizing moiety for optimum effect (i.e. preferably within 5 bases of the destabilizing moiety).

In a particular embodiment wherein the second probe, but not the first probe, comprises a destabilizing moiety (especially if the destabilizing moiety comprises a Hex dimer, as described below), the inventors have found that the presence of two adjacent unpaired bases in the second probe can increase the amount of nucleic acid produced from the promoter, but the presence of three unpaired bases can increase still further the amount of nucleic acid synthesised from the promoter.

In these embodiments the unpaired bases may be in the second probe, and may have counterpart unpaired bases in the sequence of interest (i.e. there are base mismatches). Alternatively, the bases may be unpaired because they are opposite a portion of the sequence of interest which comprises extraneous bases (present as a loop). Conversely, the unpaired bases may be present in the sequence of interest and the second probe comprises a loop of extraneous bases. Any variation from the sequence of interest which affects (increases or reduces) the number of unpaired bases in the second probe and/or the target sequence could in theory be detected although, as stated above, a variation from 1 to 2 (or vice versa) or 2 to 3 (or vice versa) in the number of unpaired bases is likely to give the greatest discrimination where the variant sequence differs by a single base from the sequence of interest. A greater number of variant bases will be more readily detected.

In a third aspect the invention provides a kit for detecting the presence of a nucleic acid target sequence of interest, the kit comprising a pair of probes in accordance with the first aspect and appropriate packaging means. The kit will typically be used for performing the method of the second aspect of the invention and conveniently comprise instructions for performing the method. The kit may advantageously comprise one or more of the following: a DNA and/or an RNA polymerase, labelling reagents, nucleotide triphosphates (labelled or otherwise), detection reagents (e.g. enzymes, molecular beacons) and buffers.

The destabilizing moiety is a chemical entity which is generally unable to undergo base pairing and hydrogen bonding in the normal manner as usually occurs when complementary strands of nucleic acid become hybridised. In the present invention the destabilising moieties effectively decrease the melting temperature (Tm) of the duplex which may be formed by the coming together of the two probes, such that in the presence of a third nucleic acid molecule (target) the molecules are able to form a much more thermodynamically stable three way junction. Hence, the presence of the destabilising moiety thermodynamically favours the three way junction over the relatively unstable probe duplex. Amplification of associated probes can then be achieved essentially as described, in detail. in WO 93/06240 (Cytocell Ltd). All manner of molecules may be suitable for use as a destabilizing moiety, although some compounds are specifically preferred, as described below. With the benefit of the present specification, the person skilled in the art will be able to test other compounds and readily select those which confer the appropriate degree of destabilization so as to prevent the hybridisation of probes in the absence of target nucleic acid of interest. Particularly preferred, as a matter of convenience, are those compounds which are commercially available in a form (e.g. as phosphoramidites) which facilitates their incorporation into synthetic oligonucleotides using conventional automated solid phase nucleic acid synthesisers.

Linker or spacer molecules have been used to introduce non-nucleotide segments into oligonucleotides. These molecules have been used to form folds and hairpins to bridge sections of oligonucleotides where no appropriate binding is possible, as well as simply to space tags further away from the oligonucleotide. A variety of such spacer molecules are available, many of which might be suitable for use as destabilizing moieties in the present invention. Such suitability could readily be ascertained by those skilled in the art with the benefit of the present disclosure.

In preferred embodiments, the first probe is such that the portion complementary to the sequence of interest ("target specific region" or "foot") is generally 10 bases or longer and the portion non-complementary to the sequence of interest ("arm region") is generally 5 bases or longer. Generally, for the first probe, the target specific region will be longer than the arm region.

The second probe has a target specific foot region, also conveniently of $\geq 10$ bases and an arm region conveniently of $\geq 20$ bases. Generally, the arm region of the second probe will be longer than the complementary arm region of the first probe, such that the second probe arm region forms an "overhand", which can act as a template for enzyme-mediated extension of the first probe in the presence of ribo- or deoxyribonucleotide triphosphates, for example as detailed in WO 93/06240. Thus, in a preferred embodiment, the 3' end of the arm region of the first probe will desirably have a 3' OH from which primer extension may be undertaken using the arm region of the second probe as template. The polymerase used to perform the extension will depend upon whether a thermal or isothermal reaction is sought. Preferably, the 3' terminus of the second probe, when composed of DNA or RNA, should be blocked to prevent chain extension. It will be apparent to those skilled in the art how this could be achieved e.g. use of a 3' phosphate, 3' propyl or a 3' dideoxynucleotide. The destabilizing moiety is typically located between the target specific region and the arm region, and may be present in the first probe and/or the second probe. Desirably the destabilizing moiety is present in the second probe. In certain applications, it may be desirable for the destabilizing moiety (additionally or alternatively) to be present in the arm region of the first probe. In some embodiments, the destabilizing moiety in one of the probes may lie partly opposite a portion of the target molecule, although this should normally be avoided.

The effects of the destabilizing moiety include: (a) reduction of background by destabilising hybridisation between the extension and template primer in the absence of target; (b) increasing target dependency through the improved control of background; and (c) release of steric compression at the three way junction and therefore assist access of polymerases. Destabilizing moieties which cannot base pair, but which nevertheless are capable of forming flexible folds and/or hairpin structures, are especially suitable. One such preferred destabilizing moiety comprises hexaethylene glycol (abbreviated herein as "Hex") (see FIG. 2), which may he present singly or in tandem up to n times (where n can be any number $\geq 1$, but conveniently has a maximum value of 5). In a particularly preferred embodiment, the arm region of the second probe comprises two Hex molecules in tandem, where the number of bases opposite the destabilising moiety in the arm region of the first probe should be six to eight bases (most preferably six), followed by a complementary region, preferably of 5–15 bases. An alternative preferred destabilizing moiety comprises a plurality of alkylene (especially methylene) repeats. Particularly preferred are penta- or hexa-methylene spacers.

Other, less preferred, destabilizing moieties may alternatively be used. These include, but are not limited to, inosine, Virazole™ (N[1]-[1-β-D ribofuranosyl] 3-carboxamido-1,2, 4,-triazole), Nebularin™ (N[9]-[1-β-D ribofuranosyl]-purine), nitropyrrole, ribose, propyl or combinations of the above eg. propyl-Hex-propyl, propyl-Hex-Hex-propyl, etc. Propyl may be replaced by, for example, ethyl, butyl, pentyl, heptyl, octyl etc. The number of bases opposite the destabilizing moiety in the arm region of the reciprocal probe should be x, where x is $\geq 1$. The exact number of bases will of course depend on the size of the destabilizing moiety and the value of n.

The following may be used as a guide: for each Hex molecule in the destabilizing moiety, the opposite oligonucleotide should preferably comprise 3–4 bases (preferably 3); for each other molecule or radical mentioned above present in the destabilizing moiety, the opposite oligonucleotide should preferably comprise a single base, with the exception of the following: butyl—two bases, pentyl—two bases, heptyl—three bases, and octyl—four bases.

The chemicals described above and used as destabilizing moieties are all commercially available (e.g. from Glen Research, USA).

In a further embodiment of the invention it may be advantageous, when seeking to detect a sequence of interest in a mixture comprising double stranded DNA (such as genomic DNA), to include in the hybridisation mixture further blocking oligonucleotides ("blocking oligonucleotides"). These blocking oligonucleotides hybridise to the sequence of interest on either side of the portion which is complementary to the first probe and the portion complementary to the second probe. The blocking oligonucleotides preferably comprise DNA, PNA, LNA (or a combination thereof) and advantageously each comprise at least 10 (more preferably at least 20) nucleotides. The purpose of the blocking oligonucleotides is to inhibit (under the hybridisation conditions employed) re-annealing of the target strand with its complementary strand. The blocking oligonucleotides may anneal to the target strand substantially adjacent to the first and second probes, or may anneal at a distance (e.g. 5–50 bases) therefrom.

Blocking oligonucleotides may offer little advantage if the first and/or second probes contain large target-complementary "feet" regions.

As mentioned above, the formation of a three way junction in accordance with the method of the invention will typically result in the de novo synthesis of nucleic acid, normally RNA. The newly-synthesised nucleic acid may be detected directly or indirectly by any of a number of techniques, preferably following an amplification step. Further details of suitable detection and amplification processes are given below.

Detection Methods

Nucleic acid produced from a three way junction in accordance with the method of the invention could be detected in a number of ways, preferably following amplification (most preferably by means of an isothermal amplification step). For example, newly-synthesised RNA could be detected in a conventional manner (e.g. by gel electrophoresis), with or without incorporation of labelled bases during the synthesis.

Alternatively, for example, newly-synthesised RNA could be captured at a solid surface (e.g. on a bead, or in i microtire plate), and the captured molecule detected by hybridisation with a labelled nucleic acid probe (e.g. radio-labelled, or more preferably labelled with an enzyme, chromophore, fluorophore and the like).

One preferred detection method involves the use of molecular beacons or the techniques of fluorescence resonance energy transfer ("FRET"), delayed fluorescence energy transfer ("DEFRET") or homogeneous time-resolved fluorescence ("HTRF"). Molecular beacons are molecules which it fluorescence signal may or may not be generated, depending on the conformation of the molecule. Typically, one part of the molecule will comprise a fluorophore, and another part of the molecule will comprise a "quencher" to quench fluorescence from the fluorophore. Thus, when the conformation of the molecule is such that the fluorophore and quencher are in close proximity, the molecular beacon does not fluoresce, but when the fluorophore and the quencher are relatively widely-separated, the molecule does fluoresce. The molecular beacon conveniently comprises a nucleic acid molecule labelled with an appropriate fluorophore and quencher.

One manner in which the conformation of the molecular beacon can be altered is by hybridisation to a nucleic acid, for example inducing looping out of parts of the molecular beacon. Alternatively, the molecular beacon may initially be in a hair-pin type structure (stabilised by self-complementary base-pairing), which structure is altered by hybridisation, or by cleavage by an enzyme or ribozyme.

FRET (Fluorescence Resonance Energy Transfer) occurs when a fluorescent donor molecule transfers energy via a nonradiative dipole—dipole interaction to an acceptor molecule. Upon energy transfer, which depends on the $R^{-6}$ distance between the donor and acceptor, the donor's lifetime and quantum yield are reduced and the acceptor fluorescence is increased or sensitised.

The inventors have used FAM (6-carboxyfluorescein) and TAMRA (N,N,N',N'-tetramethyl-6-carboxy rhodamine) as donor and acceptor in a nucleic acid hybridisation assay. The assay uses two dye labelled DNA oligomers (15 mers). FAM is linked to the 5' of one probe and TAMRA to the 3' of the other. When hybridised to target nucleic acid the probes are positioned adjacent to one another and FRET can occur. The inventors' experiments have demonstrated that for maximum signal the probes need to be spaced by five bases. Optimum spacing for DEFRET and HTRF (discussed below) may be different (often less).

Another approach (DEFRET, Delayed Fluorescence Energy Transfer) has been to exploit the unique properties of certain metal ions (Lanthanides e.g. Europium) that can exhibit efficient long lived emission when raised to their excited states ($\lambda$excitation=337 nm, $\lambda$emission=620 nm). The advantage of such long lived emission is the ability to use time resolved (TR) techniques in which measurement of the emission is started after an initial pause, so allowing all the background fluorescence and light scattering to dissipate. CY5 ($\lambda$excitation=620 nm, $\lambda$emission=665 nm) can be used as the DEFRET partner.

HTRF (see WO 92/01224 and U.S. Pat. No. 5,534,622) occurs where the donor (Europium) is encapsulated in a protective cage (cryptate) and attached to the 5' end of an oligomer. The acceptor molecule that has been developed for this system is a protein fluoropohore, called XL665. This molecule is linked to the 3' end of a second probe. This system has been developed by Packard.

In another embodiment, the newly-synthesised RNA, before or after amplification, results in formation of a ribozyme, which can be detected by cleavage of a particular nucleic acid substrate sequence (e.g. cleavage of a fluorophore/quencher-labelled oligonucleotide).

Amplification Techniques

In preferred embodiments of the present invention, the RNA derived from the target dependent transcription reaction is amplified prior to detection, the amplification step typically requiring the introduction of a DNA oligonucleotide. The amplification step is advantageously effected isothermally (i.e. without requiring thermal cycling of the sort essential in performing PCR). The introduced DNA oligonucleotide is complementary to the 3' region of the newly synthesised RNA and also contains the sequence of an RNA polymerase promoter and a unique transcribable sequence (template portion). Upon hybridisation of the newly-synthesised RNA with the DNA oligonucleotide, a primer extension reaction from the 3' end of the RNA, mediated by an added DNA polymerase, produces a functional double stranded RNA polymerase promoter. In the presence of the relevant RNA polymerase, multiple copies of a second RNA species are synthesised from the unique region of the DNA oligonucleotide. This RNA in turn can act as primer to a further round of primer extension and RNA synthesis. The synthesis of further RNA requires the presence of another DNA oligonucleotide that is complementary to the 3' region of the second RNA species. This DNA oligonucleotide also contains the sequence of an RNA polymerase promoter element together with a sequence upon transcription of which produces RNA identical to that derived in the target dependent transcription reaction. The 3' end of the RNA thus synthesised is complementary to the first DNA oligonucleotide and hence a cyclical amplification system is generated.

In a variant of the embodiment described above, the introduced DNA oligonucleotide hybridises to the de novo synthesised RNA, the respective sequences being such that a further RNA polymerase promoter is directly formed without the need for a DNA polymerase-mediated extension step. A cycling reaction may then be performed essentially as described above, with the transcript from one reaction hybridising with a DNA oligonucleotide to form a second RNA promoter, which produces a transcript having the same sequence as the original transcript.

In the above amplification strategies some background "noise" may be created because of the tendency of many RNA polymerases (at relatively low frequency) to produce RNA transcripts of a single stranded DNA sequence such that, for example, some transcription of single stranded DNA oligonucleotides may occur even in the absence of appropriate complementary strands. It is possible that this low level of background transcription can be reduced by designing the DNA oligonucleotides so as to incorporate near their 3' end a sequence which tends to cause termination of transcription. One example of such a sequence, which is especially effective at terminating T7 polymerase-mediated transcription, is AACAGAT (in the template strand), as disclosed by He et al. (1998 J. Biol. Chem. 273, 18,802). The same or a similar termination sequence could be positioned at the 5' end of the DNA template to increase processivity.

The invention will now be further described below by way of illustrative examples and with reference to the accompanying drawings in which.

FIGS. 3–8, 10, 12, and 15–18 are bar charts showing results obtained from various assay methods performed in accordance with the invention; and FIGS. 11A–11D, 13A–13C and 14A–14D are schematic representations of assay methods performed in accordance with the invention.

Figure 1:
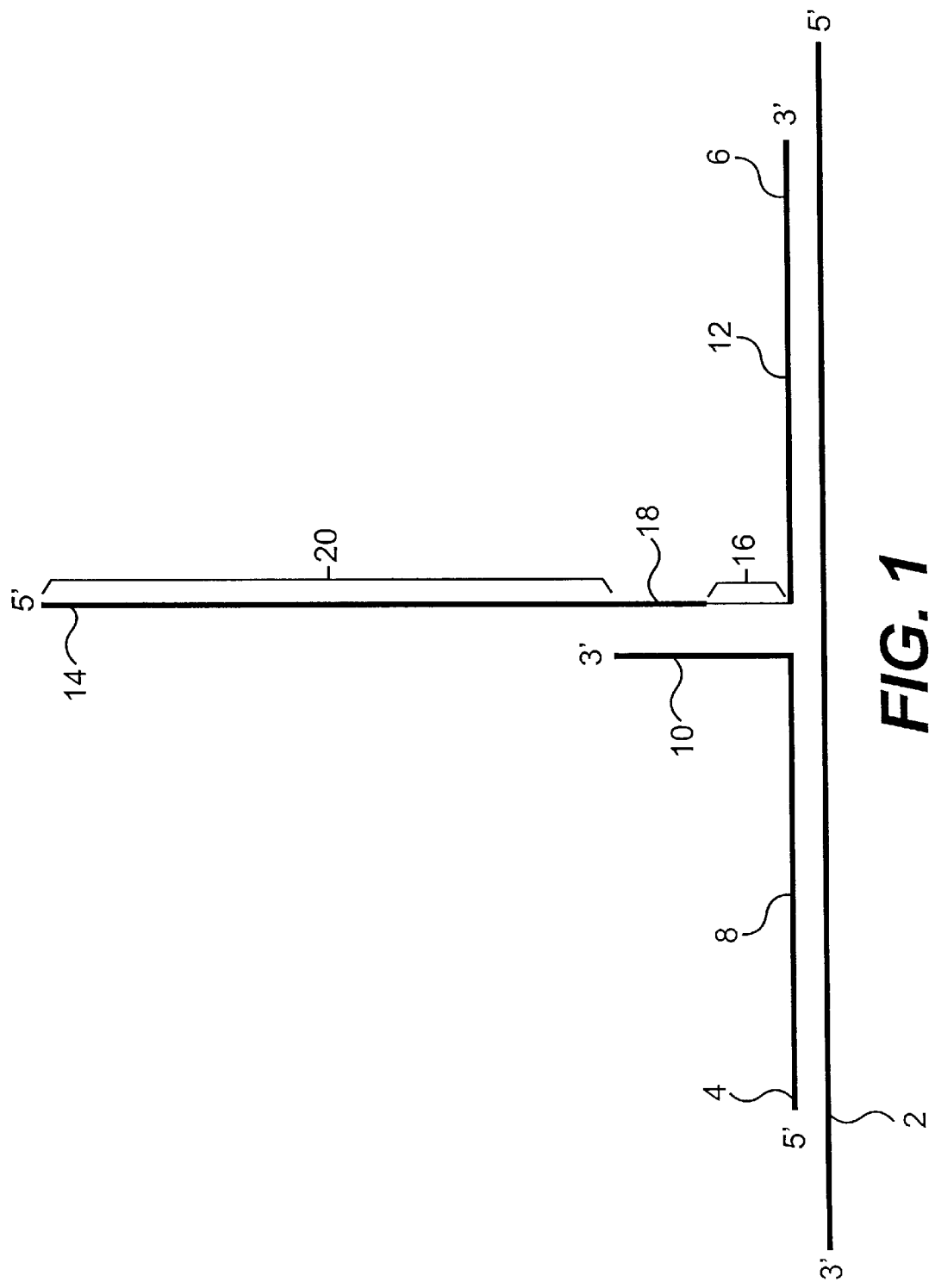
FIGS. 1 and 9 show a three way junction, with a destabilizing moiety present in the "template" second probe.
Figure 2:
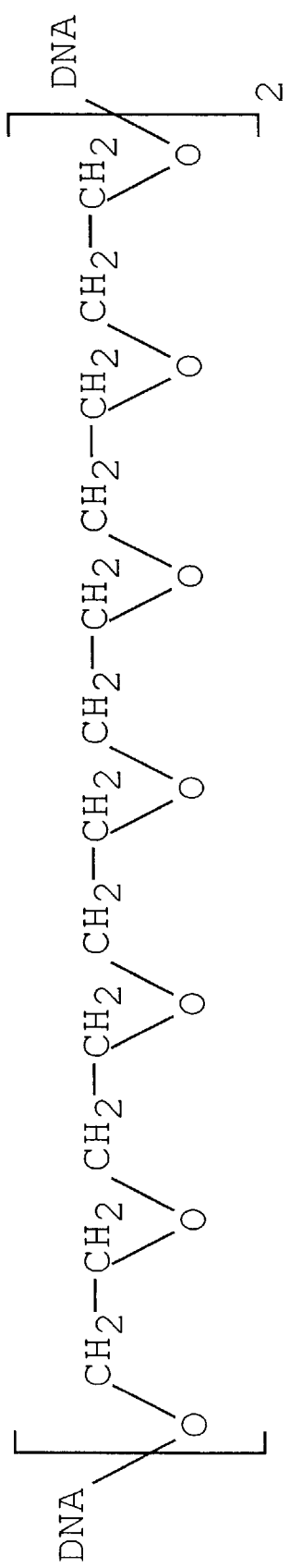
FIG. 2 shows the chemical structure of a destabilizing moiety which comprises a Hex dimer.

In FIG. 1, a three way junction is formed by hybridisation of a target sequence (2) to a first probe (4) and a second probe (6). The first probe (4) comprises a portion, the "target specific region" (8), complementary to the target sequence (2), and a portion (10) non-complementary to the target sequence which constitutes an "arm region". The second probe (6) also comprises a target specific region (12) which is complementary to a portion of the target (2) different, but substantially adjacent, to that portion of the target which hybridises to the first probe (4). The second n)robe comprises an arm region (14). The arm region (14) comprises a destabilizing moiety, denoted by reference numeral (16), located between the target specific region (12) and the rest of the arm region (14). The arm region (14) also comprises a region (18) (of between 5 and 15 bases), which is complementary to the arm region (10) of the first probe. Adjacent to the region (18) is a 5' overhang region (20), which can act as a template for extension of the 3' end of the arm region (10) of the first probe in the presence of ribo- or deoxyribonucleotide triphosphates and a suitable polymerase. The "overhang" or "template" region (20) may comprise any appropriate sequence.

For example. if amplification is to be effected by PCR or thermal cycling, virtually any sequence may be suitable. However, if amplification is to be effected by isothermal cycling (as is generally preferred), then the template region will comprise the template strand of one or more RNA polymerase promoters, and typically further comprise a +12 region adjacent to the promoter to optimise efficiency thereof, and conveniently sequences which, when transcribed, facilitate the further amplification, capture and/or detection of the transcript.

EXAMPLES

Example 1

This example demonstrates the synthesis of de novo nucleic acid as a result of the interaction of probes specific for a region of the Hepatitis B genome. Hybridisation to the target (probe 3) of first and second oligonucleotide probes results in the formation of a three way junction. The first probe is composed of two regions: a target specific region and an arm region. The second probe is also composed of two regions: a target specific region complementary to a different portion of the target than the target specific region of the first probe and an arm region which is complementary to part of the arm region of the first probe. The arm region of the second probe also contains two hexaethylene glycol (Hex) molecules incorporated in tandem. There are six bases in the first probe arm region opposite the two Hex molecules, which form a non-complementary loop opposite the Hexs. The portions of the first and second probes that are complementary to each other, but not to the target, form a nine base pair region recognised by a DNA polymerase which gives rise to probe extension under assay conditions, thus forming newly-synthesised nucleic acid. The assay mixture contains a further probe (probe 4) to amplify and enhance nucleic acid synthesis.

Preparation of Oligonucleotides

All oligonucleotide probes were synthesised by phosphoramidite chemistry using an Applied Biosystems 380A synthesiser according to the manufacturer's instructions. Hex incorporation was accomplished by reaction of the growing chain with 18-dimethoxytrityl hexaethylene glycol, 1-[(2-cyanoethyl)-(N,N-diisopropyl)]-phosphoramidite. Biotinylation of oligonucleotide probes was achieved by incorporation of a biotin phosphoramidite. Oligonucleotides functionalised with alkaline phosphatase were prepared using the manufacturer's proprietary method (Oswel). All oligonucleotides were HPLC purified using standard techniques.

Amplification of Hybridised Extended Oligonucleotide

Hybridisation was achieved in a 50 µl assay mixture that contained 20.0 pmol of first probe, 0.2 pmol of second probe, 7.5 pmol of probe 3 (Hepatitis B target) and 10.0 pmol of probe 4 (amplification probe) in 16 mM $(NH_4)_2SO_4$, 67 mM Tris-HCl pH 8.8 and 0.01% Tween-20 containing 2.5 mM $MgCl_2$, 0.2 mM of each dNTP (2'-deoxyadenosine 5'-triphosphate (dATP), 2'-deoxythymidine 5'-triphosphate (dTTP), 2'-deoxyouanosine 5'-triphosphate (dGTP) and 2'-deoxythymidine 5'-triphosphate (dCTP)). Extension and amplification was effected by 4 units of Exo(−) Polythermase™ (Bioline) DNA polymerase. Either first probe or probe 4 was biotinylated at the 5' end to enable capture on a streptavidin coated plate. The assay mixture was heated to 95° C. for 2 minutes followed by thermal cycling at 95° C. for 20 sec then 45° C. for 15 seconds for as many cycles as required to produce a measurable signal. Background values were determined for cycling in the absence of target probe.

Capture and Detection of Amplified Extended Probe

An aliquot (between 1–50 µl) of the assay mixture was transferred to the well of a 96 well streptavidin coated microtitre plate (Labsystems) containing 130 µl of 50 mM Tris-HCl pH 8.0, 138 mM NaCl, 2.7 mM KCl plus 0.1% BSA. The plate was shaken at room temperature for a minimum of 30 minutes and washed once with 50 mM Tris-HCl pH8.0 containing 138 mM NaCl, 2.7 mM KCl plus 0.1% Tween-20 (TBS/Tween-20). Next 180 µl of 150 mM NaOH/0.05% Tween-20 was added to the well and incubated at room temperature for 5 minutes with shaking. The well was washed four times with TBS/Tween-20. An alkaline phosphatase labelled oligonucleotide (probe 5) was added at a concentration 1.2 times greater than either first probe or probe 4, in a hybridisation buffer containing 50 mM Tris-HCl pH 8.0, 1M NaCl, 20 mM EDTA, 0.1% Tween-20 and 0.1% BSA. The plate was incubated at room temperature with shaking for 1 hour and washed four times with TBS/Tween-20 followed by a wash with alkaline phosphatase substrate buffer (Boehringer Mannheim). Finally, alkaline phosphatase substrate buffer containing 4-nitrophenyl phosphate (5 mg/ml) was added to each well and incubated at 37° C. for 30 minutes in a Labsystems EIA plate reader and readings taken at 405 nm.

The results (data omitted for brevity) showed that very little background signal was obtained in the absence of target, but that in the presence of the target sequence a very strong signal was obtained.

Alternative Detection System:

A europium labelled probe 5 (EG&G Wallac, Milton Keynes, UK) could alternatively be used for time-resolved fluorescence detection using the Wallac Victor 1420 multi-label counter with an excitation filter (340 nm) and emission filter (615 nm).

List of Oligonucleotides (H represents Hex)

First Probe

5' GCTCAGTTTACTACTGCCATTTGTTCGC-CCACGCGGCGGAG 3' (may be 5' biotinylated) (Seq. ID No. 11)

Second Probe

5' GGATATCACCCGATGTGCGGCGCTCCGCCG CHHAGTGGTTCGTAGGGCTTTCCCCCACTG TTT-Phosohate 3' (Seq. ID No. 12)

Probe 3 (target region of the Hetpatitis B genome).

5' AACTGAAAGCCAAACAGTGGGGGAAAGCCC TACGAACCACTGAACAAATGGCACTAGTLA ACTGAGCCAGG 3' (Seq. ID No. 13)

Probe 4

5' GGATATCACCCGATGTG 3' (may be 5' biotinylated) (Seq. ID No. 14)

Probe 5

5' TACTAGTGCCATTTG 3' (either alkaline phosphatase or europium labelled) (Seq. ID No. 15)

Example 2

The method of Example 1 was essentially repeated, this time using the human chromosome 4 and 18 alphoid repeat unit as the target, with probe sequences modified accordingly. The amplification step differed slightly in that thermal cycling was conducted using conditions of 95° C. for 20 seconds, then 55° C. for 5 seconds.

List of Oligonucleotides

First Probe

5' AAACAGAAGCATTCTCAGAAACTTCTCAGT GATGGCCCACGCGGCGGAG (may be 5' biotinylated) (Seq. ID No. 16)

Second Probe

5' GGATATCACCCGATGTGCGGCGCTCCGCCG CHHTTTGCATTCAGCTCATGGAGTTGAACACT TCC-Phosphate 3' (Seq. ID No. 17)

Probe 3 (region of the Human chromosome 4 and 18 alphoid repeat unit).

5' CTATGAAAGGAAGTGTTCAACTCCAT-GAGCTGAATGCAAACATCACT-GAGAAGTTTCTGAGAATGCTTCTGTTTGATTTT 3' (Seq. ID No. 18)

Probe 4

5' GGATATCACCCGATGTG 3' (may be 5' biotinylated) (Seq. ID No. 14)

Probe 5

5' AAACTTCTCAGTGAT 3' (alkaline phosphatase labelled) (Seq. ID No. 19)

Figure 3:
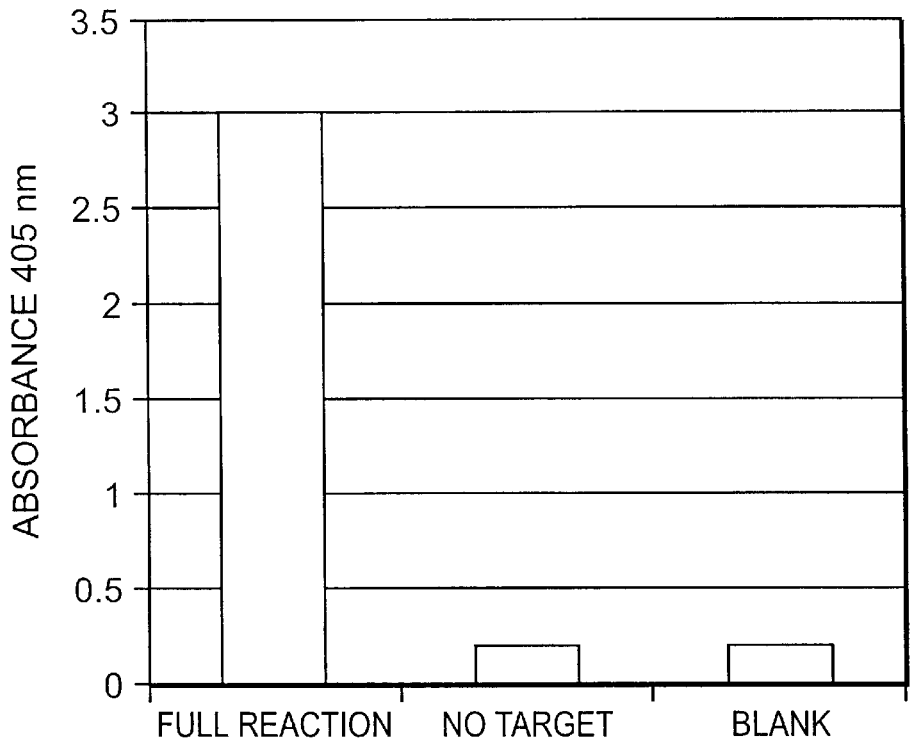

The results obtained are shown in FIG. 3, which is a bar chart showing the absorbance (at 405 nm) for the test sample in which all the necessary reagents were present (left hand bar), compared with a control sample lacking a target sequence (middle bar), or a blank sample (right hand bar).

Example 3

The method of Example 1 was essentially repeated, this time using the human Cystic Fibrosis Transmembrane Conductance Regulator (CFTR) sequence as the target, with probe sequences modified accordingly. Hybridisation conditions were altered slightly, in that the 50 µl hybridisation mixture contained 2.5 pmol of first probe, 1.0 pmol of second probe, 7.5 pmol of probe 3 (target) and 20 pmol of probe 4. Amplification was performed using thermal cycling conditions of 95° C. for 20 seconds and 60° C. for 5 seconds.

Other Detection System:

A europium labelled probe 5 (EG&G Wallac) could be used for time-resolved fluorescence detection using the Wallac Victor 1420 multilabel counter with an excitation filter (340 nm) and emission filter (615 nm).

List of Oligonucleotides

First Probe

5' TGGCACCATTAAAGAAAATATCATCTTTGC CCACCCGGCGGAG 3' (may be 5' biotinylated) (Seq. ID No. 20)

Second Probe

5' GGATATCACCCGATGTGCGGCGCTCCGCCG GHHGGTGTTTCCTATGATGAATATAGATACA GAAGCG-Phosphate 3' (Seq. ID No. 21)

Probe 3 (region of the human CFTR gene).

5' GATGACGCTTCTGTATCTATATTCATCATA GGAAACACCAAAGATGATATTTTCTTTAATGGT GCCAGGCATAATCCAGG 3' (Seq. ID No. 22)

Probe 4

5' GGATATCACCCGATGTG 3' (may be 5' biotinylated) (Seq. ID No. 14)

Probe 5

5' TAAAGAAKATATCA 3' (either alkaline phosphatase or europium labelled) (Seq. ID No. 23)

Figure 4:
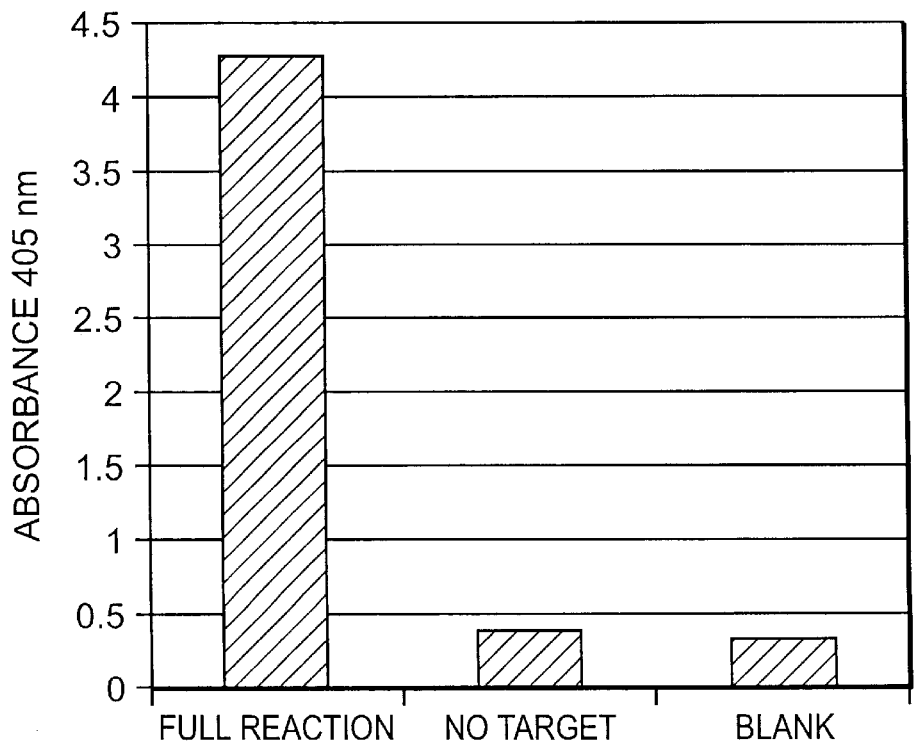

The results obtained are shown in FIG. 4, which is a bar chart showing the absorbance at 405 nm for a test sample containing, all the necessary reagents, (left hand bar), compared with a control sample lacking a target (middle bar), or a blank sample (right hand bar).

Example 4

The method of Example 3 was essentially repeated, but in this example the second probe contained two propyl groups (Pr), two hexaethylene glycol (Hex) molecules and two further propyl groups (Pr) incorporated in sequence as the destabilizing moiety.

Preparation of Oligonucleotides

Propyl incorporation was performed using a dimethoxytritylated propyl phosphoramidite. Otherwise, probes were synthesised and purified as described in the preceding examples.

List of Oligonucleotides

First Probe

5' GATTATGCCTGGCACCATTAAAGAAAATAT CATCTTTGCCCACCCGGCGGAG 3' (may be 5' biotinylated) (Seq. ID No. 24)

Second Probe (H=Hex, P=propyl)

5' GGATATCACCCGATGTGCGGCGCTCCGCCG GPPHHPPGGTGTTTCCTATGATGAATATAGATA CAGAAGCG-Phosphate 3' (Seq. ID No. 25)

Probe 3 (region of the human CFTR gene).

5' GATGACGCTTCTGTATCTATATTCATCATA GGAAACACCAAAGATGATATTTTCTTTAATGGT GCCAGGCATAATCCAGG 3' (Seq. ID No. 22)

Probe 4

5' GGATATCACCCGATGTG 3' (may be 5' biotinylated) (Seq. ID No. 14)

Probe 5

5' TTAAAGAAATATCA 3' (either alkaline phosphatase or europium labelled) (Seq. ID No. 23)

Amplification of Hybridised Extended Oligonucleotide

Hybridisation was performed using conditions as described in Example 3. Extension and amplification were performed as described previously, but with thermal cycling at 95° C. for 20 sec then 60° C. for 5 seconds.

Capture and detection of amplified extended probe was performed as described in the preceding examples.

Figure 5:
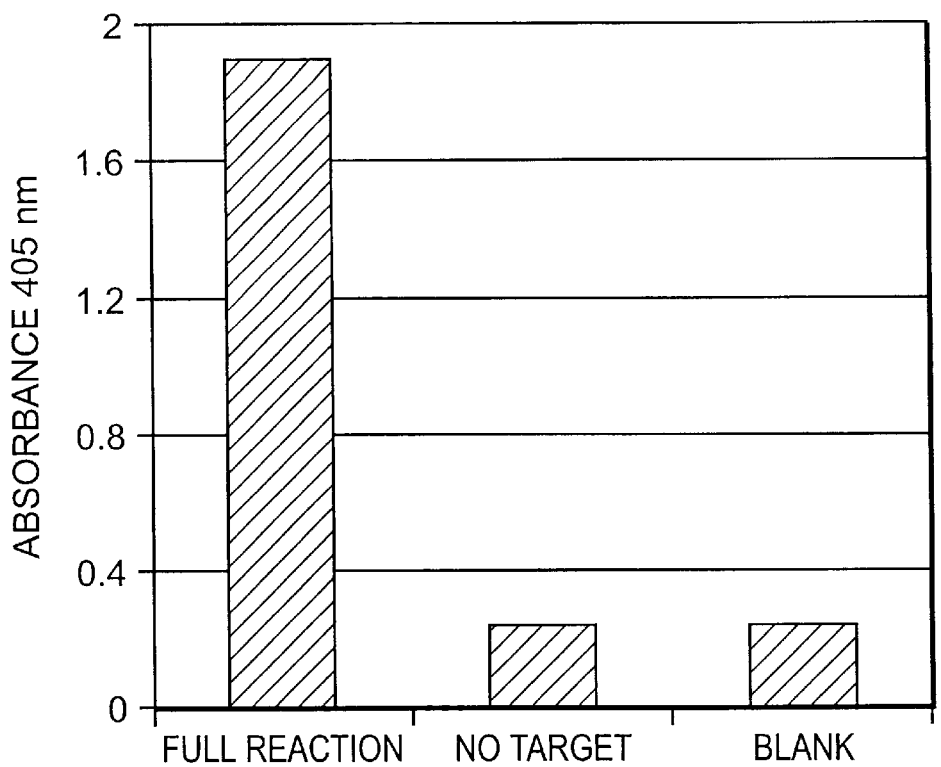

The results obtained are shown in FIG. 5, which is a bar chart showing the absorbance (at 405 nm) for the test sample in which all the necessary reagents were present (left hand bar), compared with a control sample lacking a target sequence (middle bar), or a blank sample (right hand bar). From a standard curve obtained from results using samples of known concentration, quantification of RNA can be achieved.

Example 5

This example demonstrates the synthesis of de novo nucleic acid as a result of the interaction of probes for the Human Cystic Fibrosis Transmembrane Conductance Regulator (CFTR) gene.

In this example, hybridisation to the target of first and second oligonucleotide probes results in the formation of a three way junction. The arm region of first probe contains two hexaethylene glycol (Hex) molecules incorporated in tandem as a destabilizing moiety. There are six bases in the arm region of second probe opposite the two Hex molecules, which form a non-complementary loop opposite the Hexs. The portions of first and second probes that are complementary to each other, but not complementary to the target, form a ten base pair region recognised by a DNA polymerase which gives rise to probe extension under assay conditions.

Preparation of Oligonucleotides

All oligonucleotide Tribes were synthesised and purified as described in the preceding examples.

Amplification of Hybridised Extended Oligonucleotide

Hybridisation was achieved as described in the previous examples, but using 5.0 pmol of first probe, 0.05 pmol of second probe and 7.5 pmol of probe 3 (target). Extension was effected by 4 units of Exo(–) Polythermase™ (Bioline) DNA polymerase. The first probe was biotinylated at the 5' end to enable capture on a streptavidin coated plate. The assay mixture was heated to 95° C. for 2 minutes followed by thermal cycling at 95° C. for 20 sec then 60° C. for 5 seconds for is many cycles as required to produce a measurable signal. Background values were determined for cycling in the absence of target probe.

Capture and Detection of Extended Probe

20 µl of the assay mixture was transferred to the well of a 96 well streptavidin coated microtitre plate (Labsystems) containing 130 µl of 50 mM Tris-HCl pH 8.0, 138 mM NaCl, 2.7 mM KCl plus 0.1% BSA. The plate was shaken at room temperature for a minimum of 30 minutes. The wells were then washed four times with 50 mM Tris-HCl pH 8.0 containing 138 mM NaCl, 2.7 mM KCl plus 0.1% Tween-20 (TBS/Tween-20). Anti-Dig fluorescein labelled antibody (Sigma-Aldrich) was diluted 1:10,000 in 1×STM1 (20×SSC, 0.25% Tween-20, 20% non-fat dried milk, 0.1% sodium azide) and 150 µl of antibody conjugate was added to each well prior to incubation at 37° C. for 15 minutes. The wells were washed four times with TBS/Tween-20. The sheep anti-fluorescein alkaline phosphatase (Boehringer Mannheim) was diluted 1:5,000 in 1×STM and 150 µl was added to each well prior to incubation at 37° C. for 15 minutes. The wells were then washed four times with TBS/Tween-20 followed by a wash with alkaline phosphatase substrate buffer (Boehringer Mannheim). Finally, alkaline phosphatase substrate buffer containing 4-nitrophenyl phosphate (5 mg/ml) was added to each well and incubated at 37° C. for 30 minutes. The plate was then read at 405 nm in a Labsystems EIA plate reader.

Figure 6:
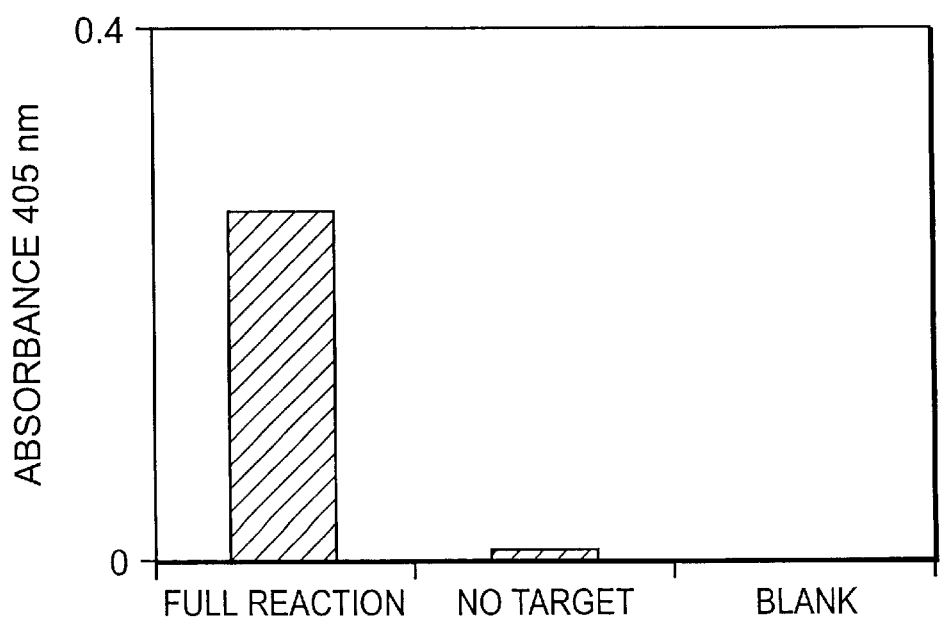

The results obtained are shown in FIG. 6, which is a bar chart showing the absorbance (at 405 nm) for the test sample in which all the necessary reagents are present (left hand bar), compared with a control sample lacking a target sequence (middle bar), or a blank sample (right hand bar).
List of Oligonucleotides
 First Probe
  5' GGCACCATTAAAGAAAATATCATCTHHCCAC CCGGCO 3' (may be 5' biotinylated) (Seq. ID No. 26)
 Second Probe
  5' GGATATCACCCGGCGGTCGTTCGTGGTTTT GCGTGCGGCGCTCCGCCGGGTGGGCGGTGT TTCCTATGATGAATATAGATACAGAAGCG- Phosphate 3' (Seq. ID No. 27)
 Probe 3 (region of the human CFTR gene).
  5' GATGACCCTTCTGTATCTATATTCATCATA GGAAACACCAAAGATGATATTTTCTTTAATGGT GCCAGGCATAATCCAGG 3' (Seq. ID No. 22)
 Probe 4
  5' GGATATCACCCG 3' (alkaline phosphatase labelled) (Seq. ID No. 28)

Example 6

This example demonstrates the synthesis of de novo ribonucleic acid as a result of the interaction of PNA:DNA chimeric probes for he gene.

Hybridisation to the target (probe 3) of first and second probes results in the formation of a three way junction. The first probe is composed of two regions: a target specific region comprised of PNA; and a DNA arm region, regions and being separated by a suitable C5 or C6 linker molecule (in this instance, 5 or 6 methylene repeats). The linker serves to provide increased flexibility between the PNA and DNA portions of the probes. The second probe also comprises two regions, separated by a C5 or C6 linker: a target specific PNA region and a DNA arm region which is in part complementary to the arm region of first probe. The arm region of second probe also contains a T7 RNA polymerase promoter sequence and sequences for capture and detection of the product. The portions of first and second probes that are complementary to each other, but not to the target, form a seven base pair region recoginised by a DNA polymerase which gives rise to probe extension under assay conditions. Extension generates a double stranded, functional promoter sequence which is recognised by a DNA-dependent RNA polymerase, leading to the target-dependent synthesis of RNA.

Preparation of Oligonucleotides

PNA is formed by coupling carboxy and amino-functionalised groups under standard conditions. PNA:DNA chimeras are formed via a C5 or C6 linker (consisting of repeating units of methylene residues). Biotinylation of oligonucleotide probes is achieved by incorporation of a biotin phosphoramidite. Otherwise, probes were synthesised and purified as described in the preceding examples.

Synthesis of RNA off Hybridised Oligonucleotide

Hybridisation is achieved in an assay mixture that contains 0.6 pmol of first probe, 50 fmol of second probe and 0.5 pmol of probe 3 (target for CFTR gene), together with T7 RNA polymerase buffer (40 mM Tris-HCl, pH 7.9, 6 mM MgCl$_2$, 2 mM spermidine, 10 mM NaCl at final concentration). The reaction volume is made up to 20 μl with RNase-free distilled water (allowing for later additions of enzymes and NTPs). Control reactions contain first and second probes but no target (probe 3). The mixture is heated to 90° C. for 3 minutes to denature the nucleic acids, cooled on ice and equilibrated to 37° C. Klenow fragment of DNA polymerase I (3'→5' exo(-) ~2.5 units) and 1 μl dNTP mix (10 mM or each dNTP: 2'-deoxyadenosinre 5'-triphosphate (dATP), 2'-deoxythymidine 5'-triphosphate (dTTP), 2'-deoxyguanosine 5'-triphosphate (dGTP) and 2'-deoxycytidine 5'-triphosphate (dCTP)), are added and the mixture incubated at 37° C. for 30 minutes to allow extension of first probe to create a functional T7 RNA polymerase promoter. T7 RNA polymerase (40 units) and 2 μl NTP mix (20 mM of each NTP: adenosine 5'-triphosphate (ATP), guanosine 5'-triphosphate (GTP), cytidine 5'-triphosphate (CTP) uridine 5'-triphosphate (UTP)) are added and the reaction is incubated at 37° C. for a further 180 minutes, prior to detection of transcribed RNA.

Capture and Detection of Synthesised RNA

DNA (portions of first and second probes, and probe 3) is removed from the assay mixture using RNase-free DNase (1.6 units DNase added per 10 μl assay mix. incubated at 37° C. for 15 minutes). Duplicate 5 μl samples of treated assay sample are added to 145 μl hybridisation buffer (50 mM Tris-HCl, pH 8.0, 1M NaCl, 20 mM EDTA and 0.1% BSA) containing 0.9 pmol probe 4 (a specific biotinylated capture oligonucleotide) and 12 pmol probe 5 (a specific, alkaline phosphatase functionalised oligonucleotide) in streptavidin coated wells. Incubation (60 minutes at room temperature, shaking at 300 rpm) allows the RNA to be immobilised on the wells via the biotinylated capture probe and to anneal to the detection probe. Unbound material is removed from the wells by washing four times with TBS/0.1% Tween-20, then once with alkaline phosphatase substrate buffer (Boehriner Mannheim). Finally, alkaline phosphatase substrate buffer containing 4-nitrophenyl phosphate (5 mg/ml) is added to each well. The plain is incubated at 37° C. in a Labsystems EIA plate reader and readings are taken at 405 nm every 2 minutes.

As before, an alternative detection system could employ a europium labelled probe 5 (EG&G Wallac) for time-resolved fluorescence detection using the Wallac Victor 1420 multilabel counter with an excitation filter (340 nm) and emission filter (615 nm).

List of Oligonucleotides
 First Probe PNA shown in lower case. DNA in upper case letters. The chosen linker (C5 or C6) is indicated by ~.
  5' aaagaaaatatcatcttt~CTGAAAT 3'
 Second Probe (PNA in lower case, DNA in upper case, ~=linker)
  5' CCTTGTCTCCGTTCTGGATATCACCCGATG TGTCTCCCTATAGTGAGTCGTATTAATTT CAG~gtgtttcctatgatg 3' (Seq. ID No.29)
 Probe 3 (region of the human CFTR gene).
  5' GATGACGCTTCTGTATCTATATTCATCATA GGAAACACCAAAGATGATATTTTCTTTAATGGT GCCAGGCATAATCCAGG 3' (Seq. ID No. 22)
 Probe 4 (capture probe)
  5' TGCCTCCTTGTCTCCGTTCT 3' (5' biotinylated) (Seq. ID No. 30)
 Probe 5 (detection probe)
  5' GGATATCACCCG 3' (either alkaline phosphatase or europium labelled) (Seq. ID No. 28)

Example 7

In this example, the target was again the CFTR gene. Both first and second probes contained a single Hex residue in their respective arm portions. The portions of the probes that are complementary to each other, but not to the target, form a ten base pair region recognised by a DNA polymerase which gives rise to probe extension under assay conditions.

Preparation of Oligonucleotides

All oligonucleotide probes were synthesised and purified as described in the preceding examples.

Amplification of Hybridised Extended Oligonucleotide

Hybridisation was performed as described in Example 5, but used a hybridisation mixture that contained 5.0 pmol of first probe, 0.05 pmol of second probe and 7.5 pmol of probe 3 (target). Extension and amplification were performed as described in Example 5. Capture and detection of extended probe were also performed substantially as described in Example 5.

Figure 7:
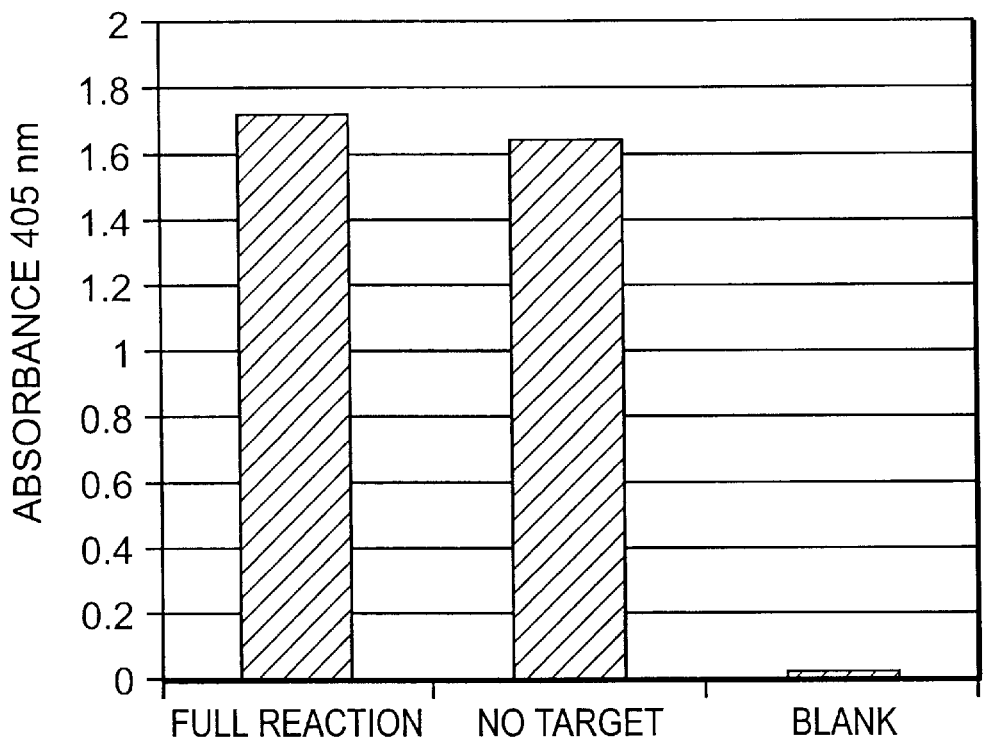

The results obtained are shown in FIG. 7, which is a bar chart showing the absorbance (at 405 nm) for the test sample in which all the necessary reagents were present (left hand bar), compared with a control sample lacking a target sequence (middle bar), or a blank sample (right hand bar), it is clear from the results that almost as much signal is generated by the sample without target, suggesting that, in this instance, inclusion of a destabilizing moiety in both first and second probes is less preferable than inclusion of the destabilizing moiety in a single probe.

List of Oligonucleotides

First Probe

5' GGCACCATTAAAGAAAATATCATCTHCCAC CCGGCG 3' (may be 5' biotinylated) (Seq. ID No. 31)

Second Probe

5' GGATATCACCCGATGTGCGGCGCTCCGCCG GGTGGHTGTTTCCTATGATGAATATAGAT ACAGAAGCG-Phosphate 3' (Seq. ID No. 32)

Probe 3 (region of the human CFTR gene).

5' GATGACGCTTCTGTATCTATATTCATCATA GGAAACACCAAAGATGATATTTTCTTTAATGGT GCCAGGCATAATCCAGG 3' (Seq. ID No. 22)

Probe 4

5' GGATATCACCCG 3' (alkaline phosphatase labelled) (Seq. ID No. 28)

Example 8

The target sequence in this example was the CFTR gene. The arrangement was such that the target non-complementary arm of the second probe comprised two hexaethylene glycol (Hex) molecules incorporated in tandem as a destabilizing moiety. There were six bases in the first probe arm, which formed a non-complementary loop opposite the Hexs. There were also two non-complementary bases in probe 3 (target) resulting from the Hex dimer continuing around the "corner" of the three way junction. The portions of first and second probes that are complementary to each other, but not to the target, formed a nine base pair region recognised by a DNA polymerase which gives rise to probe extension under assay conditions. The assay may utilise a further probe (probe 4) to amplify and enhance nucleic acid synthesis.

Preparation of Oligonucleotides

All oligonucleotide probes were synthesised and purified as described in the preceding examples.

Amplification of Hybridised Extended Oligonucleotide

Hybridisation, extension and amplification were performed exactly as described in Example 3. Capture and detection of amplified extended probe were also performed exactly as described in Example 3.

List of Oligonucleotides

First Probe

5' TTAAAGAAATATCATCTTTGCCCACCCG- GCGGAG 3' (may be 5 biotinylated) (Seq. ID No. 33)

Second Probe

5' GGATATCACCCGATGTGCGGCGCTCCGC- CGGHHTGTTTCCTATGATGAATATAGATACAG AAGCG-Phosphate 3' (Seq. ID No.34)

Probe 3 (region of the human CFTR gene).

5' GATGACGCTTCTGTATCTATATTCAT- CATAGGAAACACCAAAGAT- GATATTTTCTTfAATCCTCCAGGCATAATCCAGG 3' (Seq. ID No. 22)

Probe 4

5' GGATATCACCCGATGTG 3' (may be 5' biotinylated) (Seq. ID No. 14)

Probe 5

5' TTAAAGAAAATATCA 3' (either alkaline phosphatase or europium labelled) (Seq. ID No. 23)

Figure 8:
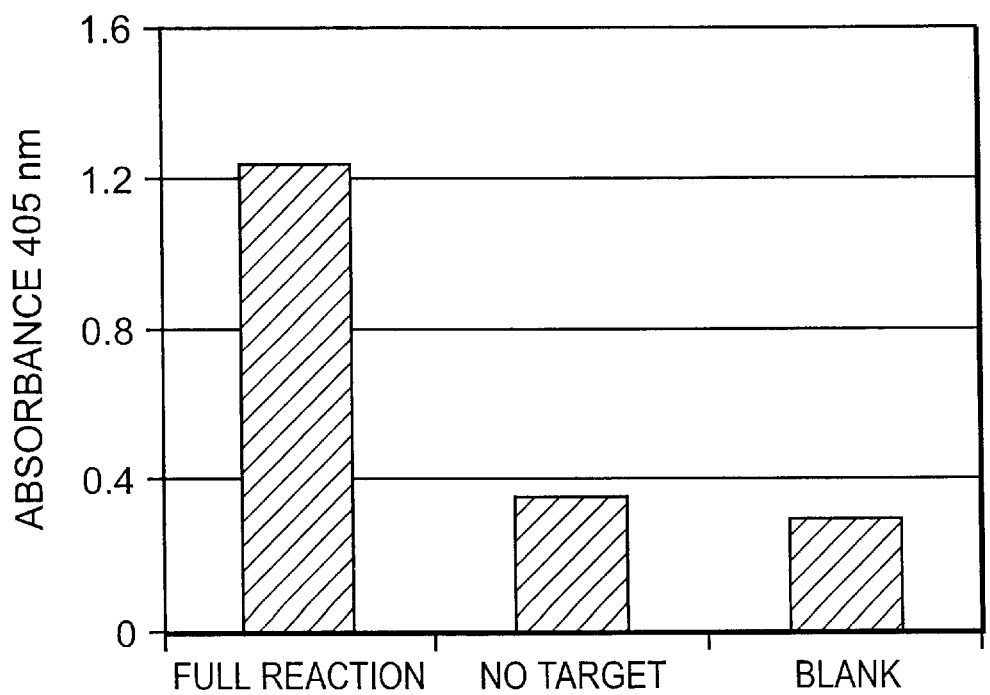

The results obtained are shown in FIG. 8 which is a bar chart showing the absorbance (at 405 nm) for the test sample in which all the necessary reagents were present (left hand bar), compared with a control sample lacking a target sequence (middle bar), or a blank sample (right hand bar).

Example 9

Figure 9:
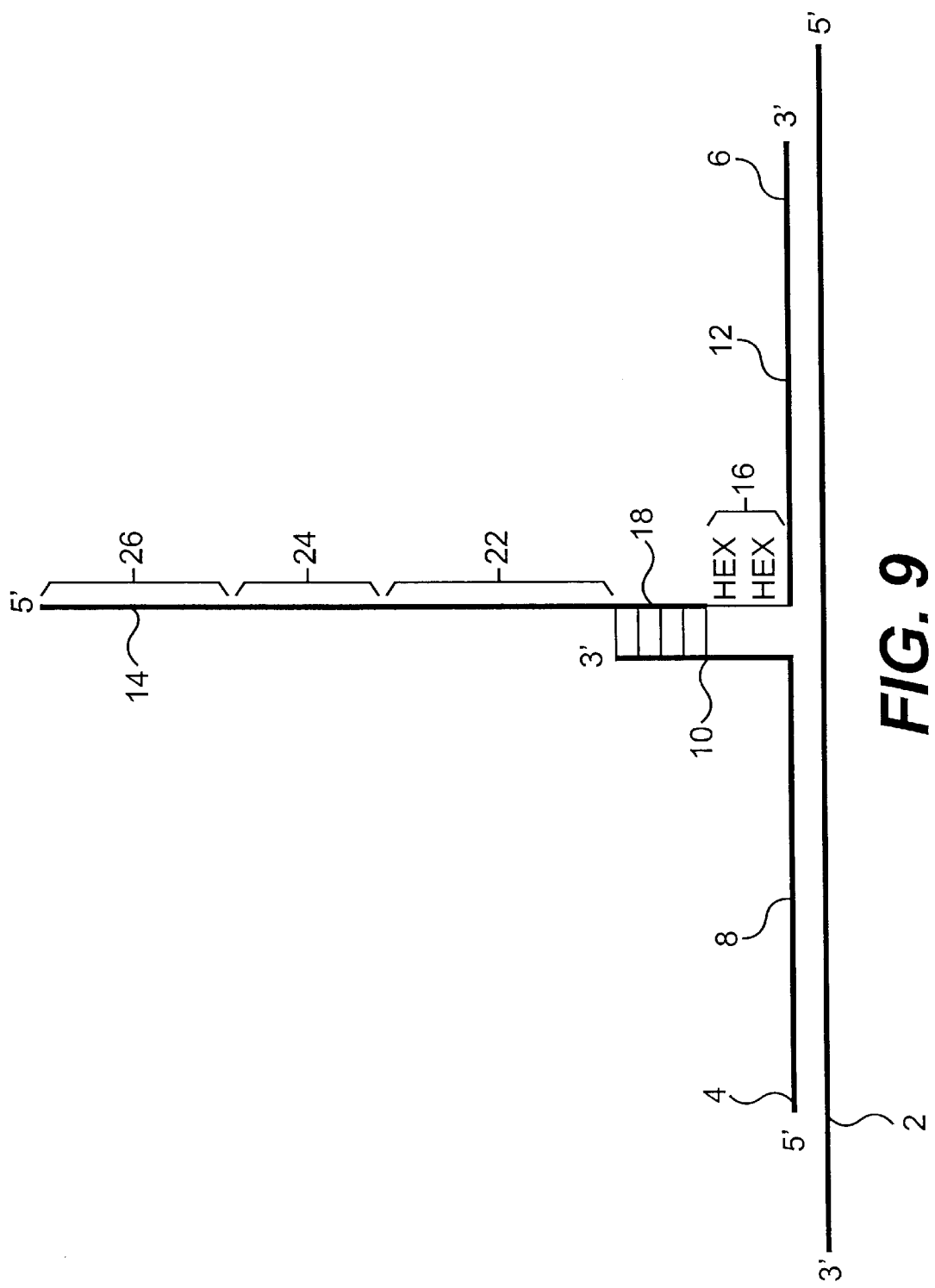

Again, in this example the target was an oligonucleotide corresponding to the sequence of the CFTR gene. The example is illustrated schematically in FIG. 9. Referring to FIG. 9, the arm (14) of second probe (6) contained two hexaethylene glycol (Hex) molecules incorporated in tandem which constituted a destabilizing moiety (16), a T7 RNA polymerase promoter sequence (22) (together with a +12 base sequence essential for optimum promoter activity and processivity Milligan et al., 1987 Nucl. Acids Res. 15, 8783–8798) and sequences for capture (26) and detection (24) of the product. There were six bases in the arm region (10) of the first probe (4) opposite the two Hex molecules, which form a non-complementary loot opposite the Hexs. The portions of the first and second probes that are complementary to each other, but not to the target, formed a five base pair region recognised by a DNA polymerase which gives rise to probe extension under assay conditions. Extension generates a double stranded, functional promoter sequence which is recognised by a DNA-dependent RNA polymerase, leading to the synthesis of RNA.

Preparation of Oligonucleotides

All oligonucleotide probes were synthesised and purified as described in the preceding examples.

Synthesis of RNA off Hybridised Oligonucleotide

Hybridisation and RNA synthesis were performed exactly as described in Example 6. Capture and detection of synthesised RNA was also performed exactly as described in Example 6.

List of Oligonucleotides

First Probe

5' GCCTGGCACCATTAAAGAAAATATCATCTT TGCCCACGAA 3' (Seq. ID No. 35)

Second Probe

5' CCTTGTCTCCGTTCTGGATATCACCCGATG TGTCTCCCTATAGTGAGTCGTATTAATTTCHHG GTGTTTCCTATGATGtATATAGATACAGAAGCG- Phosphate 3' (Seq. ID No. 36)

Probe 3 (region of the human CFTR gene).

5' GATGACGCTTCTGTATCTATATTCATCATA GGAAACACCAAAGATGATATTTTCTTTAATGGT GCCAGGCATAATCCAGG 3' (Seq. ID No. 22)

Probe 4 (capture probe)

5' TGCCTCCTTGTCTCCGTTICT 3' (5' biotinylated) (Seq. ID No. 30)

Probe 5 (detection probe)

5' GGATATCACCCG 3' (either alkaline phosphatase or europium labelled) (Seq. ID No. 28)

Figure 10:
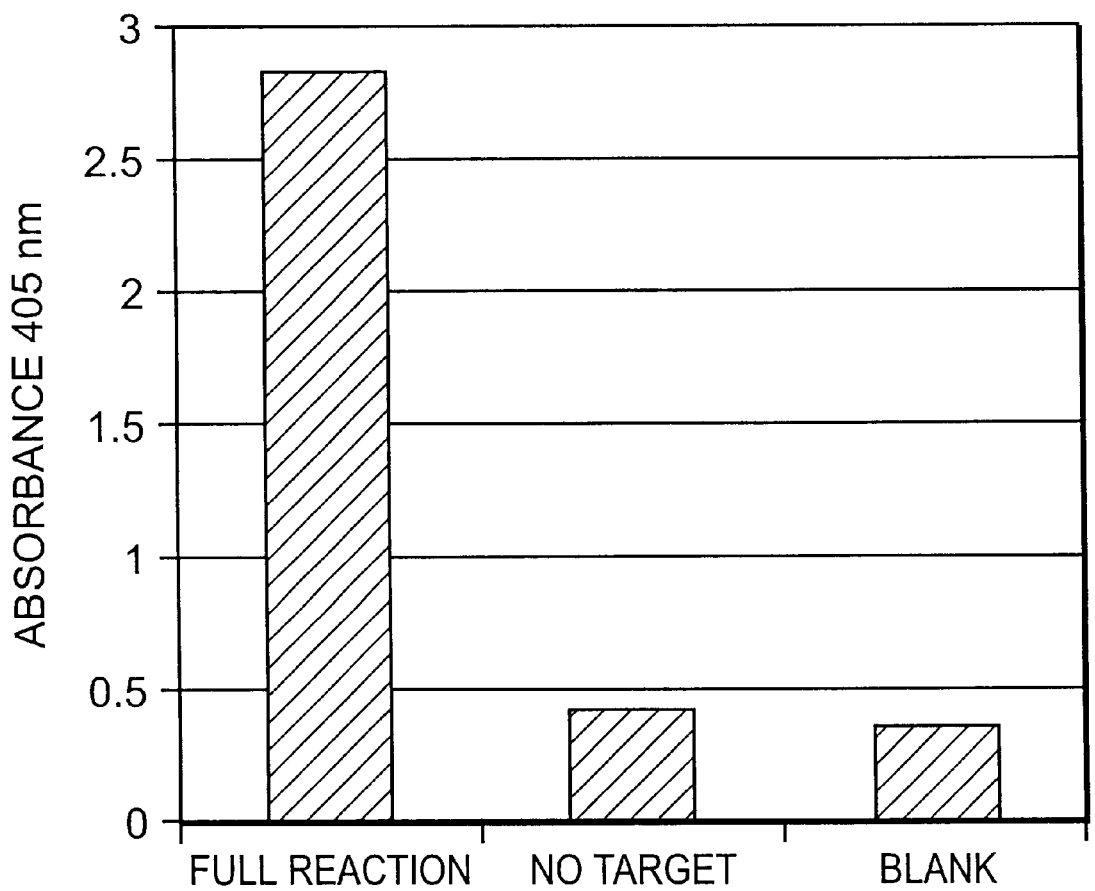

The results obtained are shown in FIG. 10, which is a bar chart showing the absorbance (at 405 nm) for the test sample in which all the necessary reagents were present (left hand bar), compared with a control sample lacking a target sequence (middle bar), or a blank sample (right hand bar).

Example 10

Unpaired Bases in the First Probe Caused by Deletions/insertions in the Target

This example demonstrates how the synthesis of de novo ribonucleic acid can be used to discriminate between wild type and mutant targets. The chosen targets were the wild type CFTR gene sequence, and the corresponding sequence with the ΔF508 mutation. An additional target, with a 2 base insertion is also listed. The mutations are detected by a decrease in signal relative to that obtained with wild type target. The example is illustrated schematically in FIGS. 11A–11D.

Figure 11A:
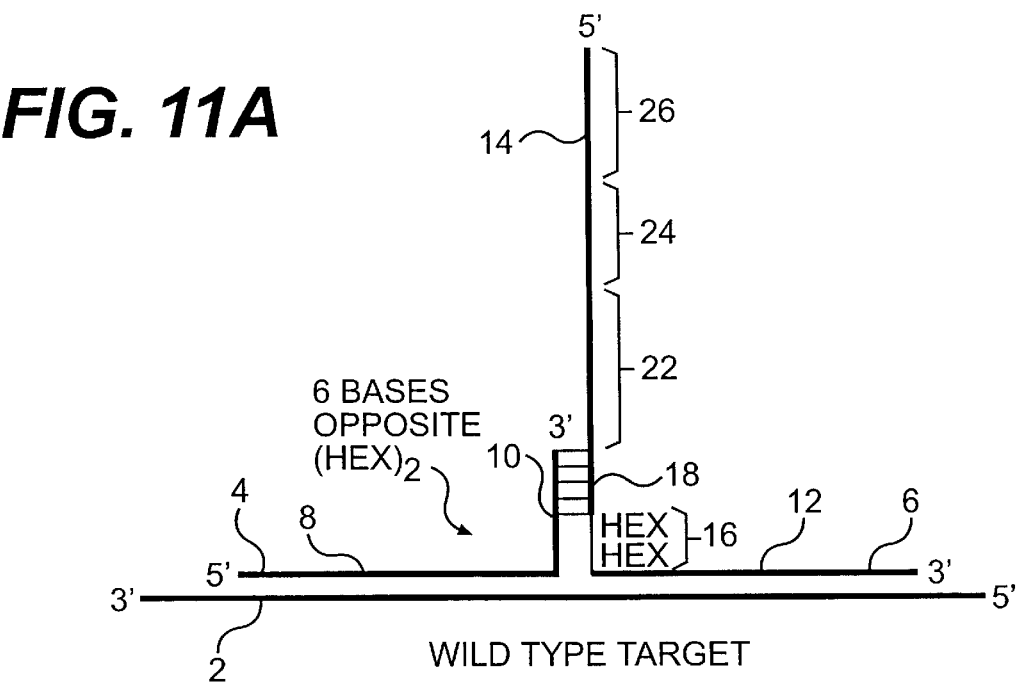
Figure 11B:
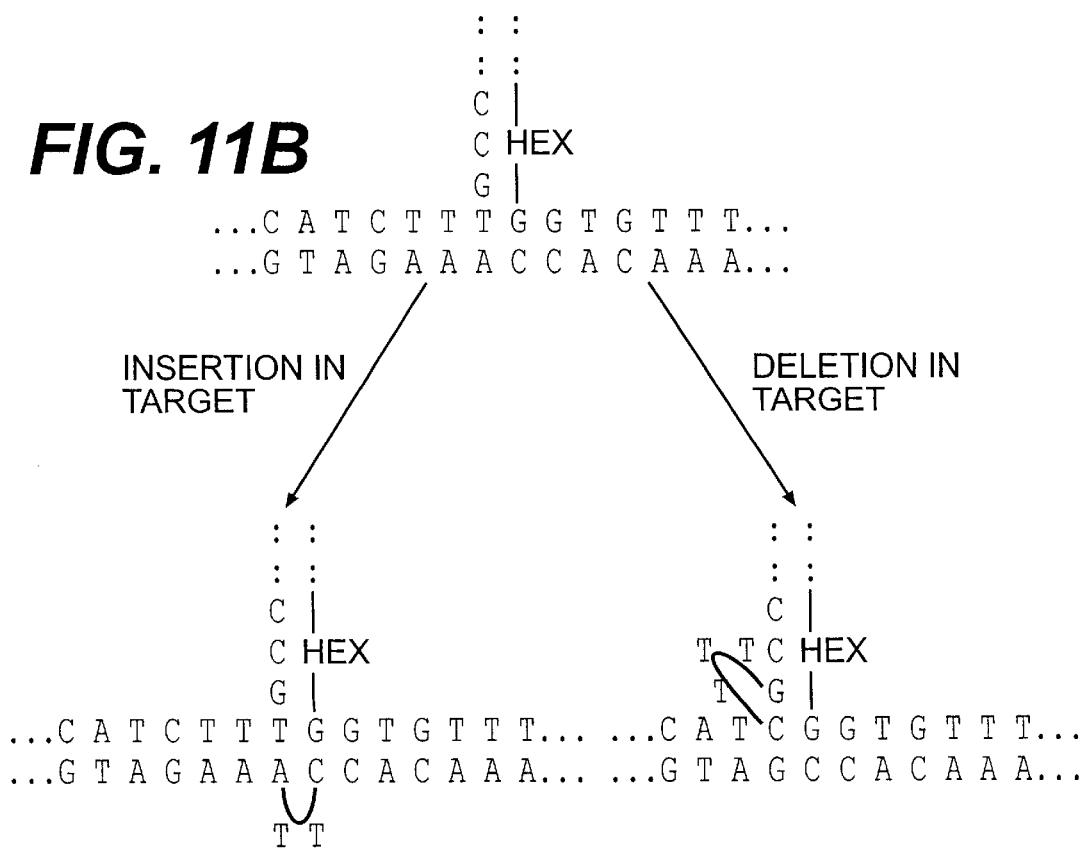

Referring to FIGS. 11A, 11B hybridisation to the wild type target (2) (probe 3a) of first and second probes (4, 6) results in the formation of a three way junction. The target specific region (8) of the first probe (4) covers the F508 region, such that region (8) forms a loop when probe (4) hybridises with the target (probe 3c) carrying a deletion (FIG. 11C). Conversely, with the mutant target carrying an insertion (probe 3b), the target forms a two base loop at the three way junction point (FIG. 11D). The arm region (14) of second probe (6) comprises two hexaethylene glycol (Hex) molecules incorporated in tandem as a destabilizing moiety (16), a T7 RNA polymerase promoter sequence (22) and sequences for capture (26) and detection (24) of the product. There are six bases in the first probe arm () opposite the two Hex molecules, which form a non-complementary loop opposite the Hexs. The portions of first and second probes that are complementary to each other, but not to the target, form a five base pair region recognised by a DNA polymerase which gives rise to probe extension under assay conditions. Extension generates a double stranded, functional promoter sequence which is recognised by a DNA-dependent RNA polymerase, leading to the synthesis of RNA.

Preparation of Oligonucleotides

All oligonucleotide probes were synthesised and purified as described in the preceding examples.

Synthesis of RNA Off Hybridised Oligonucleotide

Hybridisation (using either wild type or one of the mutant targets) and RNA synthesis were performed exactly as described in Example 6. Capture and detection of synthesised RNA were also performed exactly as described in Example 6.

List of Oligonucleotides

First Probe

5' GCCTGGCACCATTAAAGAAAATATCATCTT TGCCCACGAAAT3' (Seq. ID No. 35)

Second Probe

5' CCTTGTCTCCGTTCTGGATATCACCCGATG TGTCTCCCTATAGTGAGTCGTATTAATTTCHHG GTGTTTCCTATGATGATATAGATACAGAAGCG-Phosphate 3' (Seq. ID No.36)

Probe 3a (region of the human CFTR gene—wild type, 508 region underlined).

5' GATGACGCTTCTGTATCTATATTCATCATA GGAAACACC<u>AAA</u>GATGATATTTTCTTTTAATG GTGCCAGGCATAATCCAGG 3' (Seq. ID No. 22)

Probe 3b (region of the human CFTR gene—with 2 base insert underlined)

5' GATGACGCTTCTGTATCTATATTCATCATA GGAAACACC<u>TT</u>AAAGATGATATTTTCTTTAATG GTGCCAGGCATAATCCAGG 3' (Seq. ID No. 37)

Probe 3c (region of the human CFTR gene—with ΔF508 mutation)

5' GATGACGCTTCTGTATCTATATTCAT-CATAGGAAACACCGAATGATATTTTCTT-TAATGGTGCCAGGCATAATCCAGG 3' (Seq. ID No. 38)

Probe 4 (capture probe)

5' TGCCTCCTTGTCTCCGTTCT 3' (5' biotinylated) (Seq. ID No. 30))

Probe 5 (detection probe)

5' GGATATCACCCG 3' (either alkaline phosphatase or europium labelled) (Seq. ID No. 28)

Figure 12:
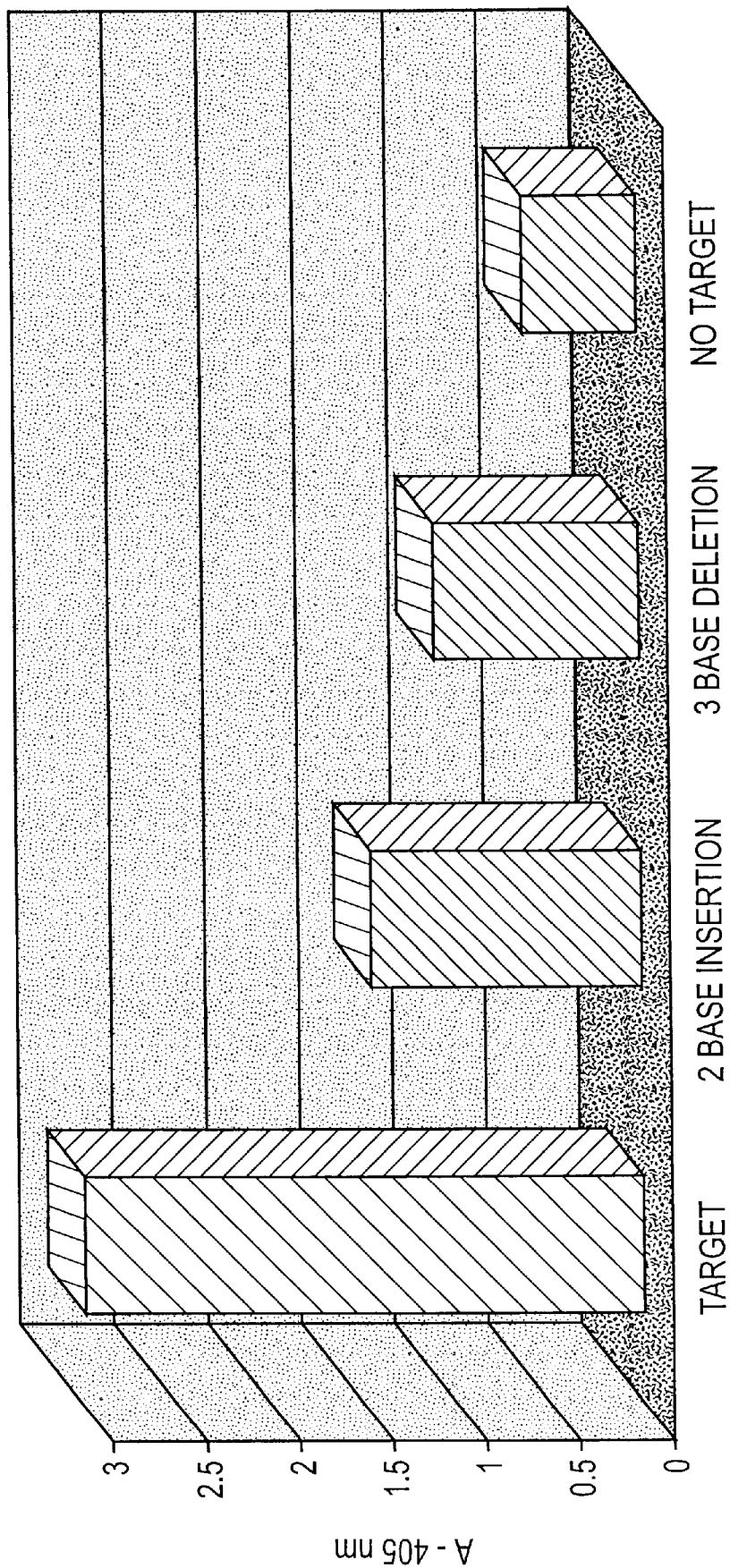

FIG. 12 illustrates a bar chart, showing the results obtained from the above example. The amount of signal generated (Absorbance at 405 nm) was highest with the wild type target sequence (extreme left hand bar), and lesser amounts of signal were obtained with the 2 base insertion mutant (mid/left hand bar) and the 3 base deletion mutant (mid/right hand bar). Very little signal (background) was generated in the absence of target (extreme right hand bar).

Example 11

Single Base Mutation Analysis Using Human GP3a Exon 10

This example demonstrates how the synthesis of de novo ribonucleic acid can be used to discriminate between targets which are wild type or carry a single base mutation. The system is designed for GP3a exon 10, to detect a single G to A mutation at position 363, but could easily be adapted to detect any single base mutation in other target sequences. The example is illustrated schematically in FIGS. 13A–13C.

Referring to FIG. 13A, hybridisation to the target (2) (probe 3a) of first and second oligonucleotide probes (4, 6) results in the formation of a three way junction. The target specific region (12) of second probe (6) hybridises to the region of GP3a exon 10 around the 363 mutation site. The arm region (14) of probe (6) comprises two hexaethylene glycol (Hex) molecules incorporated in tandem as a destabilizing moiety (16), a T7 RNA polymerase promoter sequence (22) and sequences for capture (26) and detection (24) of the product. There are six bases in the first probe arm region (10) opposite the two Hex molecules, which form a non-complementary loop opposite the Hexs. The portions of first and second probes (4, 6) that are complementary to each other, but not to the target form, a five base pair region recognised by a DNA polymerase which gives rise to probe extension under assay conditions. Extension generates a double stranded, functional promoter sequence which is in turn recognised by a DNA-dependent RNA polymerase, leading to the synthesis of RNA.

Discrimination is achieved by designing the target specific region of second (6) probe so that it forms a 2 base loop when it hybridises with wild type target (FIG. 13B). The single G to A base change means that a bigger 3 base, loop out forms upon hybridisation with the mutant target, causing a change in signal (FIG. 13C).

Preparation of Oligonucleotides

All oligonucleotide probes are synthesised and purified as described in the preceding examples.

Synthesis of RNA off Hybridised Oligonucleotide

Hybridisation (using either the wild type or mutant target sequence) and RNA synthesis is performed exactly as described in Example 6. Capture and detection of synthesised RNA is also performed exactly as described in Example 6.

List of Oligonucleotides

First Probe

5' GGGCTGACCCTCCCGGGGGCTGCGC-CCACGAAAT 3' (Seq. ID No. 39)

Second Probe

5' CCTTGTCTCCGTTCTGGATATCACCCGATGTGT CTCCCTATAGTGAGTCGTATTAATTTCHHACTCT CGTCCTGCTGGGAAGGGCGATAGT-Phosphate 3' (Seq. ID No. 40)

Probe 3a (region of GP3a exon 10—wild type, position of base altered in probe 3b underlined).

5' TGAGTGCTCAGAGGAGGACTATCGCCCTTC CCAGCAGGACGA<u>G</u>TGCAGCCCCGGGACGG TCAGCCCGTCTGCAGCCAGCGGGGCGAGTGCC TCT 3' (Seq. ID No. 41)

Probe3b (region of GP3a exon 10—position of G to A mutation underlined)

5' TGAGTGCTCAGAGGAGGACTATCGCCCTTC CCAGCAGGACGA<u>A</u>TGCAGCCCCGGGAGGG TCAGCCCGTCTGCAGCCAGCGGGGCGAGT GCCTCT 3' (Seq. ID No. 42)

Probe 4 (capture probe)

5' TGCCTCCTTGTCTCCGTTCT 3' (5' biotinylated) (Seq. ID No. 30) Probe 5 (detection probe)

5' GGATATCACCCG 3' (either alkaline phosphatase or europium labelled) (Seq. ID No. 28)

Example 12

Unpaired Bases in the Second Probe Caused by Deletions/insertions in the Target This example demonstrates how the synthesis of de novo ribonucleic acid can be used to discriminate between wild type and mutant targets. The chosen targets were the gene, with or without various base deletions or changes. In this example, the mutations are detected by an increase in generated signal relative to that provided by the wild type target. The example is illustrated schematically in FIG. 14.

Referring to FIG. 14A, hybridisation to the target (2) (probe 3a) of first and second oligonucleotide probes (4, 6) results in the formation of a three way junction in which the foot region of second probe is fully base-paired with the target (FIG. 14B). The target specific region (12) of second probe (6) covers the region of the target (2) which may include a 2 or 3 base deletion: the probe (6) therefore forms a two or three base loop when it hybridises with a mutant target (FIGS. 14C, D). The arm region (14) of probe (6) comprises two hexaethylene glycol (Hex) molecules incorporated in tandem, as a destabilizing moiety (16), a T7 RNA polymerase promoter sequence (22) and sequences for at capture (26) and detection (24) of the product. There are six bases in the first probe arm region (10) opposite the two Hex molecules, which form a non-complementary loop opposite the Hexs. The portions of probes (4) and (6) that are complementary to each other, but not to the target, form a five base pair region recognised by a DNA polymerase which gives rise to probe extension under assay conditions. Extension generates a double stranded, functional promoter sequence which is recognised by a DNA-dependent RNA polymerase, leading to the synthesis of RNA.

Preparation of Oligonucleotides

All oligonucleotide probes were synthesised and purified as described in the preceding examples.

Synthesis of RNA off Hybridised Oligonucleotide

Hybridisation (using either the wild type target [probe 3a], or one of the mutant targets [probes 3b–3d] and RNA synthesis were performed exactly as described in Example 6. Capture and detection of synthesised RNA was performed exactly as described in Example 6.

List of Oligonucleotides

First Probe (extension probe)

5' GCCTGGCACCATTAAAGAAAATATCAT CTTTGCCCACGAAAT 3' (Seq. ID No. 35)

Second Probe (template probe)

5' CCTTGTCTCCGTTCTGGATATCACCCGATGT GTCTCCCTATAGTGAGTCGTATTAATTTCHHGG TGTTTCCTATGATGAATATAGATACAGAAGCG-Phosphate 3' (Seq. ID No. 36)

Probe 3a (region of the human CFTR gene—wild type, region of bases deleted or changed in other probes underlined).

5' GATGACGCTTCTGTATCTATATTCATCATA GGAAA<u>CAC</u>CAAAGATGATATTTTCTTMAAT GGTGCCAGGCATAATCCAGG 3' (Seq. ID No. 22)

Probe 3b (region of human CFTR gene—with 3 base deletion at site marked ↓)

↓
5' GATGACGCTTCTGTATCTATATTCATCATAGGAAACAAAGATGATATTTT

CTTTAATGGTGCCAGGCATAATCCAGG 3' (Seq. ID No. 43)

Probe 3c (region of human CFTR gene with 2 base deletion at site marked ↓)

↓
5' GATGACGCTTCTGTATCTATATTCATCATAGGAAACAAAGATGATAT

TTTCTTTAATGGTGCCAGGCATAATCCAGG 3' (Seq. ID No. 44)

Probe 3d (region of human CFTR gene, differing from probe 3c by a single C to A base change, marked ↓)

↓
5' GATGACGCTTCTGTATCTATATTCATCATAGGA<u>A</u>AACAAAGATGATAT

TTTCTTTAATGGTGCCAGGCATAATCCAGG 3' (Seq. ID No. 45)

Probe 4 (capture probe)

5' TGCCTCCTTGTCTCCGTTCT 3' (5' biotinylated) (Seq. ID No. 30)

Probe 5 (detection probe)

5' GGATATCACCCG 3' (either alkaline phosphatase or europium labelled) (Seq. ID No. 28)

Figure 15:
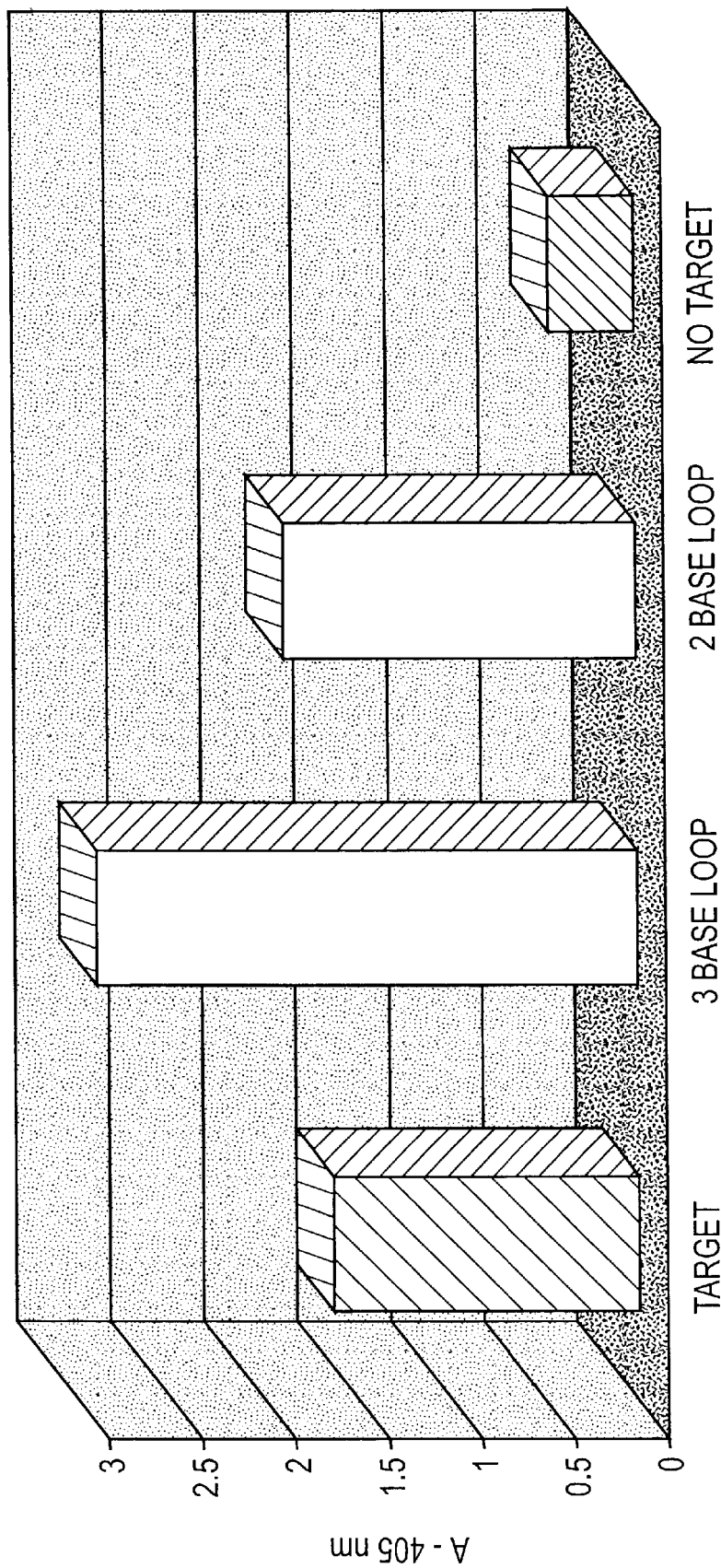

FIG. 15 is a bar chart showing results obtained from the above example. The amount of signal generated (Absorbance at 405 nm) was shown to be target-dependent. For the wild type target (extreme left hand bar) a much greater signal was obtained than for the background signal present in the "no target" control (extreme right hand bar). However, the presence of a mutation in the target, which caused the formation of a two base loop in the second probe upon hybridisation to the target (mid/right hand bar) unexpectedly caused an increase in signal. Even more surprisingly, the amount of signal was increased further still by use of a mutant target which caused the formation of a three base loop in the second probe (mid/left hand bar).

Example 13

Transcription From a Three Way Junction to Form a Ribozyme

This example demonstrates the synthesis of de novo ribonucleic acid as a result of the interaction of probes for the Human CFTR gene. The RNA produced has the sequence of a known ribozyme (Clouet-D'Orval & Uhlenbeck 1996, RNA 2: 483–491) and can bind to a dual labelled single stranded oligonucleotide to form a functional ribozyme. Cleavage of the labelled oligonucleotide (molecular beacon) at a specific site will then generate a signal.

Hybridisation to the target (probe 3) of two oligonucleotide probes results in the formation of a three way junction. The first probe is composed of two regions: a target specific region and an arm region. The second probe is similarly composed of a target specific region and an arm region which is in part complementary to the arm region of the first probe. The arm of the second probe also comprises two hexaethylene glycol (Hex) molecules incorporated in tandem, a T7 RNA polymerase promoter sequence, a 12 bp sequence to optimise transcription efficiency and a sequence for the production of a ribozyme, allowing for end detection of signal. There are six bases in the first probe opposite the two Hex molecules, which form a non-complementary loop opposite the Hexs.

The portions of the first and second probes that are complementary to each other, but not to the target, form an eight base pair overlap required for recognition by a DNA polymerase which gives rise to probe extension under assay conditions. Extension generates a double stranded, functional promoter sequence which is recognised by a DNA-dependent RNA polymerase, leading to the synthesis of RNA (using the second probe as template) which has the sequence of a ribozyme. The RNA produced then anneals to an RNA oligonucleotide (probe 4) which is double-labelled with a fluorophore and quencher. Ribozyme activity cleaves probe 4, separating the fluorophore from the quencher, so producing a signal.

Preparation of Oligonucleotides

All oligonucleotide probes are synthesised and purified as described in the previous examples. Fluorophore and quencher molecules are attached to oligonucleotides by manufacturer's proprietary methods (Oswel).

The ribozyme substrate RNA oligonucleotide may be protected from cleavage by contaminating RNases (likely to be present in clinical samples) by the incorporation of suitable NTP analogues. Biotinylation of oligonucleotide probes is achieved by incorporation of a biotin phosphoramidite.

Synthesis of RNA off Hybridised Oligonucleotide

Hybridisation is achieved in an assay mixture that contains 0.2 pmol of first probe, 50 fmol of second probe and 50 fmol of probe 3 (target for CFTR gene), together with T7 RNA polymerase buffer (40 mM Tris-HCl, pH 7.9, 6 mM $MgCl_2$, 2 mM spermidine, 10 mM NaCl at final concentration). The reaction volume is made up to 20 µl with RNase-free distilled water (allowing for later additions of enzymes and NTPs). Control reactions contain first and second probes, but no target (probe 3).

The mixture is heated to 90° C. for 3 minutes to denature the nucleic acids, then cooled (by ramping at 0.1° C./second) to 10° C. Bst DNA polymerase (~8 units), 1 µl dNTP mix (0.1 mM of each dNTP: 2'-deoxyadenosine 5'-triphosphate (dATP), 2'-deoxythymidine 5'-triphosphate (dTTP), 2'-deoxyguanosine 5'-triphosphate (dGTP) and 2'-deoxycytidine 5'-triphosphate (dCTP)), T7 RNA polymerase (40 units) and 2 µl NTP mix (20 mM of each NTP: adenosine 5'-triphosphate (ATP), guanosine 5'-triphosphate (GTP), cytidine 5'-triphosphate (CTP) uridine 5'-triphosphate (UTP)) are added and the mixture is incubated at 37° C. for 3 hours. This allows the extension of the first probe to create a functional T7 RNA polymerase promoter. The promoter is recognised by T7 RNA polymerase and RNA is generated by transcription.

Detection of Synthesised RNA

DNA is removed from the assay mixture using RNase-free DNase (1.6 units DNase added per 10 µl assay mix, incubated at 37° C. for 10 minutes, heated at 90° C. for 3 minutes and cooled to 15° C.). Duplicate 5 µl samples of a suitable dilution of the treated assay sample are added to 100 µl buffer (50 mM Tris -HCl pH7.5, 20 mM $MgCl_2$, 10% ethanol), followed by 10 pmol of probe 4 (double-labelled RNA, 5'-Tamra, 3'-Fam) which is the ribozyme substrate. The target-dependent RNA product of the three way junction is designed to be the corresponding "hammerhead" ribozyme. Probe 4 anneals to the RNA product, creating a functional ribozyme. Ribozyme cleavage of the substrate, which separates the quencher from the fluorophore, can be monitored by fluorescence detection (Fam excitation at 485 nm, emission at 535 nm). Alternatively, substrate cleavage could be measured by a change in fluorescence polarisation. Since substrate turnover is possible (50 substrate molecules may be cleaved by a single ribozyme), a level of amplification may be achieved during the detection process.

Alternative Real Time Detection System

Real time detection would be possible if the ribozyme substrate molecule is present in the extension/transcription reaction mixture in suitable buffer conditions.

Alternative Detection Systems

The RNA product could include a capture sequence, allowing it to be captured on to a streptavidin-coated well via a biotinylated capture probe. After wash steps to remove unbound material, probe 4 could be added and ribozyme cleavage could be monitored as described above.

Alternative labels could be attached to the ribozyme substrate molecule.

List of Oligonucleotides

First Probe (extension probe)

5' GCCTGGCACCATTAAAGAAAATATCATCTT TGCCCACTTCGAAAT 3' (Seq. ID No. 46)

Second Probe (template probe)

5' GAATCTCATCAGTAGCGAGCTCTCTCTCCC TATAGTGAGTCGTATTAATTTCGAAHHGGTGTT TCCTATGATGAATATAGATACAGAAGCG-Phosphate 3' (Seq. ID No. 47)

Probe 3

5' GATGACGCTTCTGTATCTATATTCATCATA GGAAACACCAAAGATGATATTTTCTTTAATGGT GCCAGOCATAATCCAGG3' (Seq. ID No. 22)

Probe 4 (ribozyme substrate)

5' Tamra-GAAUCGAAACGCGAAAGCGUCUAG CGU-Fam 3' (Seq. ID No. 48)

Example 14

Detection of Deletion Mutations in Target Nucleic Acid

This example demonstrates how discrimination between the wild type CFTR gene and a target with a 3 base deletion (Δ507, which causes cystic fibrosis) may be achieved, using probes which are PNA/DNA chimeras.

The target complementary portions of the first and second probes consist of PNA, and the target non-complementary portions consist of DNA. The PNA and DNA portions of the respective probes are joined by a hexamethylene (first probe) or pentamethylene (second probe) linker, which linkers act as destabilizing moieties in accordance with the invention.

The DNA arm of the second probe also contains a T7 RNA polymerase promoter sequence, a 12 bp sequence to optimise transcription efficiency, and sequences for capture and detection of the product.

The portions of probes one and two that are complementary to each other but not to the target form a seven base pair overlap required for recognition by a DNA polymerase which gives rise to probe extension under assay conditions. Extension generates a double stranded, functional promoter sequence which is recognised by the T7 DNA-dependent RNA polymerase, leading to the synthesis of RNA.

Mutation discrimination is achieved because the interaction between the first and second probes and the target is much less efficient with the mutant target (probe 4) than with the wild type (probe 3).

Preparation of Oligonucleotides

DNA oligonucleotide probes were synthesised as described previously. PNA oligonucleotides were prepared using the manufacturers proprietary method (PNA Diagnostics, Copenhagen, Denmark). To form chimeras, PNA and DNA oligonucleotides were joined via a penta- or hexa-methylene linker by proprietary methods. Biotinylation of oligonucleotide probes was achieved by incorporation of a biotin phosphoramidite. Oligonucleotides functionalised with alkaline phosphatase were prepared using the manufacturer's proprietary method (Oswel). All oligonucleotides were HPLC purified using standard techniques.

Synthesis of RNA off Hybridised Oligonucleotide

Hybridisation was achieved in an assay mixture that contained 0.2 pmol of first probe, 50 fmol of second probe and 50 fmol of probe 3 or probe 4 (targets) conditions otherwise being as described in Example 6. The hybridisation mixture was heated to 90° C. for 3 minutes to denature the nucleic acids, cooled by ramping (0.1° C./second) to 47° C., then held at 47° C. With the sample still at 47° C., Bst DNA polymerase (8 units) and 1 µl dNTP mix (10 mM of each dNTP: 2'-deoxyadenosine 5'-triphosphate (dATP), 2'-deoxythymidine 5'-triphosphate (dTTP), 2'-deoxyguanosine 5'-triphosphate (dGTP) and 2'-deoxycytidine 5'-triphosphate (dCTP)), were added. The mixture was incubated at 47° C. for 30 minutes to allow extension of probe 1 to create a functional T7 RNA polymerase promoter. The sample temperature was reduced to 37° C., T7 RNA polymerase (40 units) and 2 µl NTP mix (20 mM of each NTP: adenosine 5'-triphosphate (ATP), guanosine 5'-triphosphate (GTP), cytidine 5'-triphosphate (CTP) and uridine 5'-triphosphate (UTP)) were added and the reaction was incubated at 37° C. for a further 180 minutes, prior to detection of transcribed RNA.

Capture and detection of synthesised RNA were performed as described in Example 6.

Figure 16:
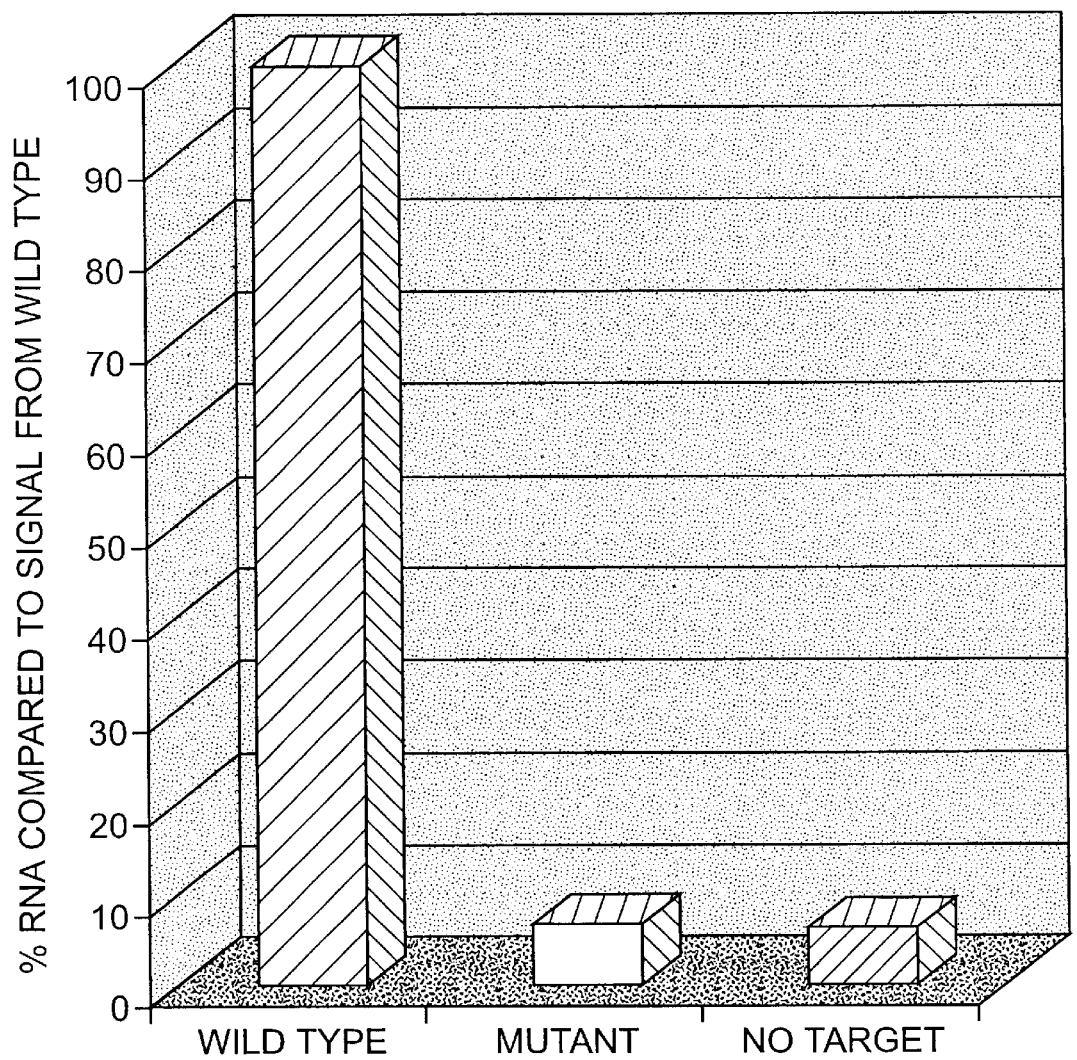

The results obtained are illustrated in FIG. 16, which is a bar chart showing percentage of RNA produced relative to the amount produced in the presence of wild type target. The wild type target (left hand column), by definition, produces 100% RNA. In contrast, the amount of RNA produced by mutant target (middle column) or in the control (no target, right hand column), was about 5%.

List of Oligonucleotides

Capitals denote DNA, lower case letters PNA. $C_6$ or $C_5$ indicates the hexa- or penta-methylene linker joining the two regions.

First Probe (extension probe)

agaaaatatcatcttt-$C_6$-5'CTGAAAT3'

Second Probe (template probe)

5' TGCCTCCTTGTCTCCGTTCTGGATAT-CACCCGATGTGTCTCCTATAGT-GAGTCGTATTAATTTCAG3' $C_5$-ggtgtttcctatgatg (Seq. ID No. 49)

Probe 3 (target—wild type). The 3 bases which have been deleted from probe 4 are shown underlined.

5' GATGACGCTTCTGTATCTATATTCAT-CATAGGAAACACCAAA GATGATATTTTCTTTAATGGTGCCAGGCATAATCCAGG 3' (Seq. ID No. 22)

Probe 4 (target—deletion mutant). Sequence is identical to probe 3, except that 3 bases have been deleted (from position marked by an arrow), to mimic the Δ507 mutation causing cystic fibrosis. The deleted region lies under the extension oligonucleotide foot, 3 bases away from the junction site in the three way junction.

↓
5' GATGACGCTTCTGTATCTATATTCATCATAGGAAACACCAAAGATATT

TTCTTTAATGGTGCCAGGCATAATCCAGG 3' (Seq. ID No. 51)

Probe 5 (capture probe)

5' TGCCTCCTTGTCTCCGTTCT 3' (5' biotinylated) (Seq. ID No. 30)

Probe 6 (detection probe)

5' GGATATCACCCG 3' (either alkaline phosphatase or europium labeled) (Seq. ID. No. 28)

Example 15

Detection of SNPs in Target Nucleic Acid

This example uses chimeric PNA/DNA probes to distinguish between single base substitutions in target nucleic acids. As with the preceding example, first and second probes contained target-complementary PNA portions, joined by $C_6$ or $C_5$ linkers to a non target complementary DNA portion.

The DNA arm of the second probe also contained a T7 RNA polymerase promoter sequence, a 12 bp sequence to optimise transcription efficiency, and sequences for capture and detection of the product. The portions of the first and second probes that are complementary to each other but not to the target form a seven base pair overlap required for recognition by a DNA polymerase which gives rise to probe extension under assay conditions. Extension generates a double-stranded functional promoter sequence which is recognised by the T7 DNA-dependent RNA polymerase, leading to the synthesis of RNA.

Mutation discrimination is achieved because the interaction between first and second probes and the target is less efficient with the mutant target (probes 4, 5 or 6) compared to the wild type target (probe 3).

All oligonucleotides were prepared as described in the preceding example.

Synthesis of RNA from Hybridised Oligonucleotide

Hybridisation was achieved in an assay mixture that contained 0.6 pmol of first probe, 50 fmol of second probe and 0.5 pmol of probe 3, 4, 5 or 6 (targets), together with T7 RNA polymerase buffer. Further processing (DNA extension, transcription, and capture and detection of RNA product) was performed as described in Example 14.

List of Oligonucleotides

Capitals denote DNA, lower case letters PNA. $C_6$ or $C_5$ indicates the hexa- or penta-methylene linker joining the PNA\DNA.

First Probe (extension probe)

gaaaatatcatcttt -$C_6$-5' CTGAAAT3'

Second Probe (template probe)

5' TGCCTCCTTGTCTCCGTTCTGGATATCACC CGATGTGTCTCCCTATAGTGAGTCGTATTAATTT CAG3' -$C_5$-ggtgtttcctatgatg (Seq. ID No. 49)

Probe 3 (target—wild type).

5' GATGACGCTTCTGTATCTATATTCATCATA GGAAACACCAAAGATGATATTTTCTTTAATGGT GCCAGGCATAATCCAGG 3' (Seq. ID No. 22)

Probe 4 (target with single base substitution). Sequence is identical to probe 3, except that a single base has been changed (position underlined). The mutation lies under the template foot, 10 bases from the junction site of the three way junction.

5' GATGACGCTTCTGTATCTATATTCATCAT <u>C</u>GGAAACACCAAAGATGATATTTTCTTTAATGG TGCCAGGCATAATCCAGG 3' (Seq. ID No. 51)

Probe 5 (target—with single base substitution). Sequence is identical to probe 3, except that a single base has been changed (position underlined). The mutation lies under the extension foot, 8 bases from the junction site of the three way junction.

5' GATGACGCTTCTGTATCTATATTCATCATA GGAAACACCAAAGATG<u>C</u>TATTTTCTTTAATGGT GCCAGGCATAATCCAGG 3' (Seq. ID No. 52)

Probe 6 (target—with single base substitution). Sequence is identical to probe 3, except that a single base has been changed at each of the two positions altered in probes 4 and 5 (positions underlined).

5' GATGACGCTTCTGTATCTATATTCATCATC GGAkACACCAAAGATG<u>C</u>TATTTTCTTTAATGGT GCCAGGCATAATCCAGG 3' (Seq. ID No. 53)

Probe 7 (capture probe)

5' TGCCTCCTTGTCTCCGTTCT 3' (5' biotinylated) (Seq. ID No. 30)

Probe 8 (detection probe)

5' GGATATCACCCG 3' (either alkaline phosphatase or europium labeled) (Seq. ID No. 28)

Figure 17:
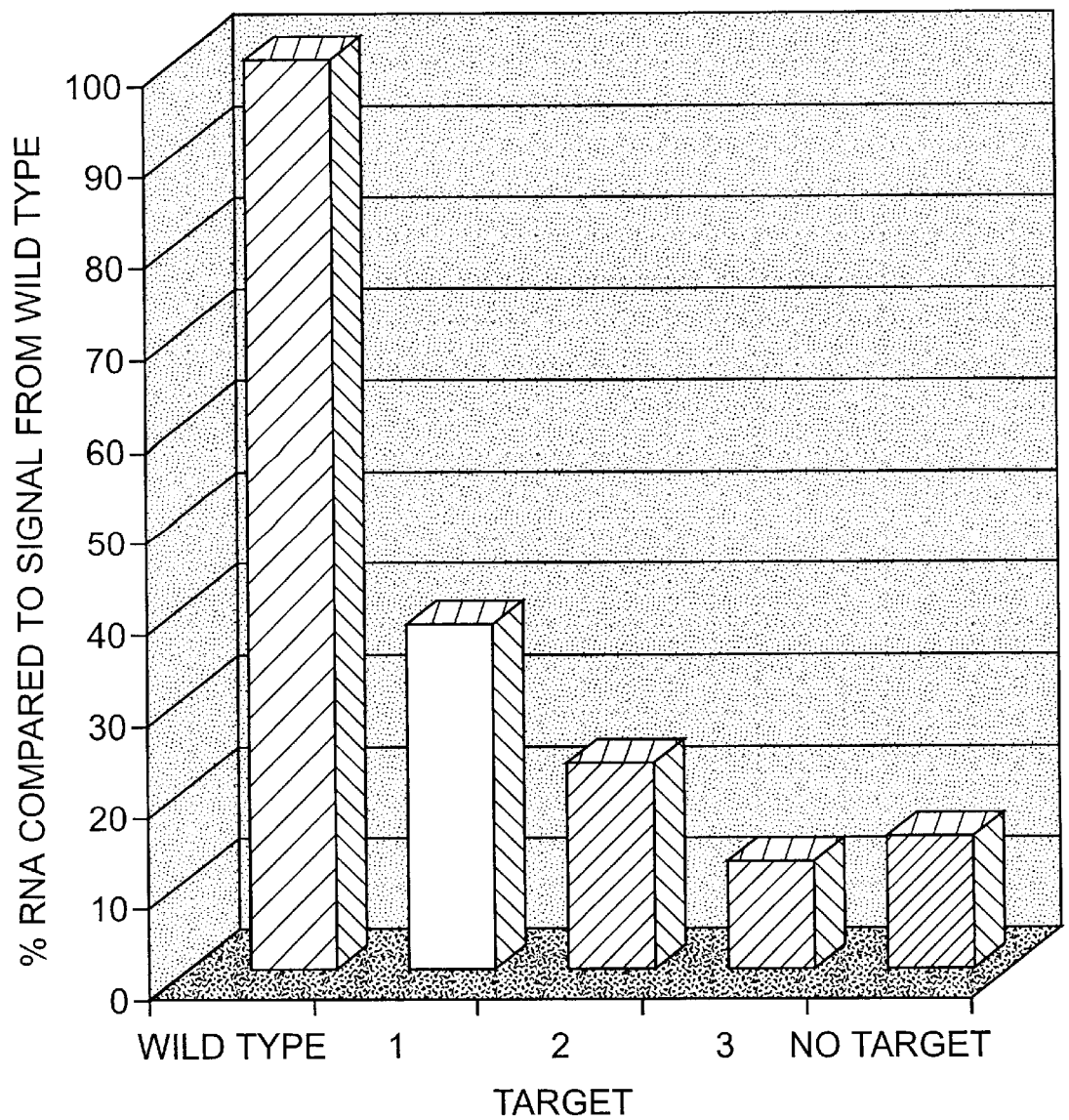

The results obtained are illustrated in FIG. 17, which is a bar chart showing % of RNA produced relative to the amount produced in the presence of wild type target. The wild type target (left hand column), by definition, produces 100% RNA. In contrast, significantly less RNA is produced with any of the mutant targets (columns labelled 1, 2 and 3) or in the control (no target, right hand column).

Example 16

Optimised Extension/transcription at a Three Way Junction

This example relates to optimisation of certain assay conditions. In effect, Example 9 was repeated using the identical probes employed in that example, although assay conditions were essentially as described in Example 14. Extension of the hybridised template probe (second probe) was conducted using a high or a low concentration of dNTPs, as described below.

Synthesis of RNA off Hybridised Oligonucleotide

Hybridisation was performed in an assay mixture that contained 0.2 pmol of first probe, 50 fmol of second probe and 50 fmol of probe 3 (target for CFTR gene), as described in Example 14. However, extension with Bst DNA polymerase (8 units), was performed using 1 μl dNTP mix of either 0.1 mM or 10 mM dNTPs. Transcription was performed as described in Example 14. Capture and detection of synthesised RNA was then performed, again as described in example 14. Typical results are shown in FIG. 18.

Figure 18:
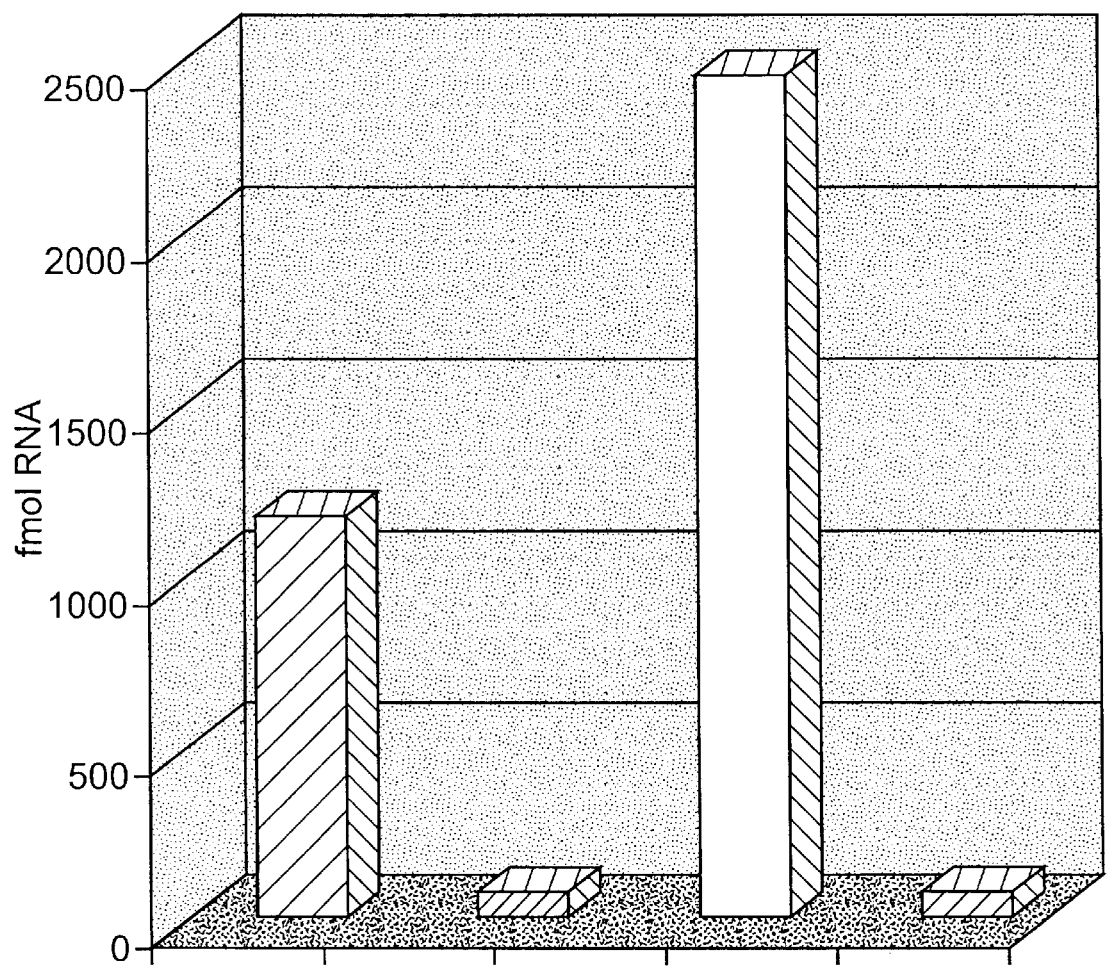

FIG. 18 is a bar chart showing amount of RNA produced (in fMol) in the presence (columns 1 and 3) or absence of target at high (500 μM) concentrations (columns 1 and 2) or low (5 μM) concentrations (columns 3 and 4) of dNTPs. In the absence of target, virtually no RNA is produced, whilst appreciable amounts are produced in the presence of target, at either dNTP concentration. However, significantly more (over two-fold increase) RNA is produced at the lower dNTP concentration. It appears that too high a concentration of dNTPs can inhibit the RNA polymerase. A concentration of around 1–10 μM may well be nearly optimal for the dNTPs in this type of assay.

What is claimed is:

1. A method of detecting a nucleic acid sequence of interest in a sample, the method comprising (a) contacting the sample with first and second probes, wherein the first probe comprises a portion complementary to the sequence of interest and so capable of hybridizing thereto, and a portion non-complementary to the sequence of interest, and wherein the second probe comprises a portion complementary to the sequence of interest and so capable of hybridizing thereto, and a portion non-complementary to the sequence of interest but complementary to that portion of the first probe which is non-complementary to the sequence of interest, such that the first and second probes are capable of hybridizing to the sequence of interest in an adjacent or substantially adjacent manner, so as to allow complementary portions of the first and second probes to hybridize to each other; (b) causing extension of the first probe with a nucleic acid polymerase, using the second probe as a template; and (c) detecting directly or indirectly the extension of the first probe, so as to indicate the presence of the sequence of interest; wherein the first and/or second probe comprises a destabilizing moiety which cannot base pair with the reciprocal probe, thereby preventing hybridization of the first and second probes in the absence of the sequence of interest, and wherein the destabilizing moiety does not comprise nucleic acid base.

2. A method according to claim 1, wherein the first and second probes comprise DNA, RNA, PNA (peptide nucleic acid), LNA (locked nucleic acid) or any combination thereof.

3. A method according to claim 1, wherein the destabilizing moiety comprises hexaethylene glycol, pentamethylene or hexamethylene.

4. A method according to claim 1, wherein the destabilizing moiety is present in the second probe.

5. A method according to claim 1, wherein the sequence of the first or second probe is such that hybridisation to the sequence of interest forms a loop of unpaired nucleic acid bases in the first or second probe and/or in the sequence of interest.

6. A method according to claim 5, wherein hybridisation of the first or second probe to the sequence of interest forms a loop of two or three unpaired nucleic acid bases in the first or second probe, and/or in the sequence of interest.

7. A method according to claim 1 comprising a control reaction in which the first and second probes are contacted with a control nucleic acid having a known nucleic acid sequence.

8. A method according to claim 1, wherein extension of the first probe results in formation of an active nucleic acid promoter.

9. A method according to claim 8, wherein extension of the first probe results in formation of a T3, T7 or SP6 RNA polymerase promoter, which allows for transcription of multiple RNA copies of at least part of the second probe.

10. A method according to claim 8, wherein detection of nucleic acid synthesised from the active nucleic acid promoter allows for indirect detection of extension of the first probe.

11. A method according to claim 8, wherein transcription caused by the active nucleic acid promoter results in synthesis of a nucleic acid sequence having ribozyme activity.

12. A method according to claim 1, wherein nucleic acid is subjected to an amplification process prior to detection.

13. A method according to claim 1, wherein nucleic acid synthesised as a direct or indirect result of extension of the first probe is detected by hybridisation with a further nucleic acid probe.

14. A method according to claim 13, wherein the further nucleic acid probe comprises a molecular beacon.

15. A method according to claim 1 wherein nucleic acid, synthesised as a direct or indirect result of extension of the first probe, is captured at a solid surface.

16. The method of claim 1, wherein the destabilizing moiety is covalently linked to the first or second probe.

17. A pair of nucleic acid probes for use in a method of detecting a nucleic acid sequence of interest, first probe of the pair comprising a portion complementary to the sequence of interest and so capable of hybridizing thereto and a portion non-complementary to the sequence of interest, and a second probe of the pair comprising a portion complementary to the sequence of interest and so capable of hybridizing thereto and a portion non-complementary to the sequence of interest but complementary to that portion of the first probe which is non-complementary to the sequence of interest, such that the first and second probes are capable of hybridizing to the sequence of interest in an adjacent or substantially adjacent manner so as to allow complementary portions of the first and second probes to hybridize to each other, wherein the first and/or second probe comprises a destabilizing moiety which cannot base pair with the reciprocal member of the pair of probes, thereby preventing hybridization of the first and second probes in the absence of the sequence of interest, and wherein the destabilizing moiety does not comprise a nucleic acid base.

18. A pair of probes according to claim 17, for use in a method according to claim 1.

19. A kit for use in detecting the presence in a sample of a nucleic acid sequence of interest, the kit comprising a pair of probes in accordance with claim 17, and appropriate packaging means.

20. A kit according to claim 19, further comprising instructions for use in performing the method of claim 1.

21. A kit according to claim 19, further comprising one or more of the following: a DNA polymerase; an RNA polymerase; ribo- or deoxyribo-nucleotide triphosphates (labelled or unlabelled); labelling reagents; detection reagents; buffers.

* * * * *

SEQUENCE LISTING (1) GENERAL INFORMATION:

(iii) NUMBER OF SEQUENCES: 53

(2) INFORMATION FOR SEQ ID NO: 1:

(i) SEQUENCE CHARACTERISTICS:
      (A) LENGTH: 12 base pairs
      (B) TYPE: nucleic acid
      (C) STRANDEDNESS: single
      (D) TOPOLOGY: linear (xi) SEQUENCE DESCRIPTION: SEQ ID NO : 1:

ATCGTCAGTC CC (2) INFORMATION FOR SEQ ID NO: 2:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO : 2:

GCTCTCTCTC CC                                               12

(2) INFORMATION FOR SEQ ID NO: 3:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO : 3:

ATCCTCTCTC CC                                               12

(2) INFORMATION FOR SEQ ID NO: 4:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO : 4:

GTTCTCTCTC CC                                               12

(2) INFORMATION FOR SEQ ID NO: 5:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO : 5:

GATGTGTCTC CC                                               12

(2) INFORMATION FOR SEQ ID NO: 6:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO : 6:

GTTGTGTCTC CC                                               12

(2) INFORMATION FOR SEQ ID NO: 7:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO : 7:

ATCCTCGTGC CC                                               12

(2) INFORMATION FOR SEQ ID NO: 8:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO : 8:

```
GCTCTCGTGC CC                                                   12
```

(2) INFORMATION FOR SEQ ID NO: 9:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO : 9:

```
GTTCTCGTGC CC                                                   12
```

(2) INFORMATION FOR SEQ ID NO: 10:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO : 10:

```
GTTGTGGTGC CC                                                   12
```

(2) INFORMATION FOR SEQ ID NO: 11:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 11:

```
GCTCAGTTTA CTAGTGCCAT TTGTTCGCCC ACGCGGCGGA G                   41
```

(2) INFORMATION FOR SEQ ID NO: 12:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (xi) SEQUENCE DESCRIPTION: SEQ ID NO: 12:

```
GGATATCACC CGATGTGCGG CGCTCCGCCG CNNAGTGGTT CGTAGGGCTT T CCCCCACTG   60

TTT                                                             63
```

(2) INFORMATION FOR SEQ ID NO: 13:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO: 13:

```
AACTGAAAGC CAAACAGTGG GGGAAAGCCC TACGAACCAC TGAACAAATG G CACTAGTAA   60
```

```
ACTGAGCCAG G                                                          71

(2) INFORMATION FOR SEQ ID NO: 14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 14:

GGATATCACC CGATGTG                                                    17

(2) INFORMATION FOR SEQ ID NO: 15:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 15:

TACTAGTGCC ATTTG                                                      15

(2) INFORMATION FOR SEQ ID NO: 16:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO: 16:

AAACAGAAGC ATTCTCAGAA ACTTCTCAGT GATGGCCCAC GCGGCGGAG                  49

(2) INFORMATION FOR SEQ ID NO: 17:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (xi) SEQUENCE DESCRIPTION: SEQ ID NO: 17:

GGATATCACC CGATGTGCGG CGCTCCGCCG CNNTTTGCAT TCAGCTCATG G AGTTGAACA     60

CTTCC                                                                 65

(2) INFORMATION FOR SEQ ID NO: 18:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (xi) SEQUENCE DESCRIPTION: SEQ ID NO: 18:

CTATGAAAGG AAGTGTTCAA CTCCATGAGC TGAATGCAAA CATCACTGAG A AGTTTCTGA    60

GAATGCTTCT GTTTGATTTT                                                 80

(2) INFORMATION FOR SEQ ID NO: 19:

(i) SEQUENCE CHARACTERISTICS:
        (A) LENGTH: 15 base pairs
        (B) TYPE: nucleic acid
        (C) STRANDEDNESS: single
```

(D) TOPOLOGY: linear (xi) SEQUENCE DESCRIPTION: SEQ ID NO: 19:

AAACTTCTCA GTGAT                                                                15

(2) INFORMATION FOR SEQ ID NO: 20:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO: 20:

TGGCACCATT AAAGAAAATA TCATCTTTGC CCACCCGGCG GAG                                  43

(2) INFORMATION FOR SEQ ID NO: 21:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (xi) SEQUENCE DESCRIPTION: SEQ ID NO: 21:

GGATATCACC CGATGTGCGG CGCTCCGCCG GNNGGTGTTT CCTATGATGA A TATAGATAC              60

AGAAGCG                                                                         67

(2) INFORMATION FOR SEQ ID NO: 22:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (xi) SEQUENCE DESCRIPTION: SEQ ID NO: 22:

GATGACGCTT CTGTATCTAT ATTCATCATA GGAAACACCA AAGATGATAT T TTCTTTAAT              60

GGTGCCAGGC ATAATCCAGG                                                           80

(2) INFORMATION FOR SEQ ID NO: 23:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO: 23:

TTAAAGAAAA TATCA                                                                15

(2) INFORMATION FOR SEQ ID NO: 24:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (xi) SEQUENCE DESCRIPTION: SEQ ID NO: 24:

GATTATGCCT GGCACCATTA AAGAAAATAT CATCTTTGCC CACCCGGCGG A G                      52

(2) INFORMATION FOR SEQ ID NO: 25:

(i) SEQUENCE CHARACTERISTICS:

(A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO: 25:

GGATATCACC CGATGTGCGG CGCTCCGCCG GNNNNNNGGT GTTTCCTATG A TGAATATAG          60

ATACAGAAGC G                                                               71

(2) INFORMATION FOR SEQ ID NO: 26:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO: 26:

GGCACCATTA AGAAAATAT CATCTNNCCA CCCGGCG                                    37

(2) INFORMATION FOR SEQ ID NO: 27:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (xi) SEQUENCE DESCRIPTION: SEQ ID NO: 27:

GGATATCACC CGGCGGTCGT TCGTGGTTTT GCGTGCGGCG CTCCGCCGGG T GGGCGGTGT         60

TTCCTATGAT GAATATAGAT ACAGAAGCG                                            89

(2) INFORMATION FOR SEQ ID NO: 28:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (xi) SEQUENCE DESCRIPTION: SEQ ID NO: 28:

GGATATCACC CG                                                              12

(2) INFORMATION FOR SEQ ID NO: 29:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (xi) SEQUENCE DESCRIPTION: SEQ ID NO: 29:

CCTTGTCTCC GTTCTGGATA TCACCCGATG TGTCTCCCTA TAGTGAGTCG T ATTAATTTC         60

AG                                                                         62

(2) INFORMATION FOR SEQ ID NO: 30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 30:

TGCCTCCTTG TCTCCGTTCT                                                      20

(2) INFORMATION FOR SEQ ID NO: 31:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO: 31:

```
GGCACCATTA AAGAAAATAT CATCTNCCAC CCGGCG                              36
```

(2) INFORMATION FOR SEQ ID NO: 32:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO: 32:

```
GGATATCACC CGATGTGCGG CGCTCCGCCG GGTGGNTGTT TCCTATGATG A ATATAGATA   60
CAGAAGCG                                                             68
```

(2) INFORMATION FOR SEQ ID NO: 33:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO: 33:

```
TTAAAGAAAA TATCATCTTT GCCCACCCGG CGGAG                               35
```

(2) INFORMATION FOR SEQ ID NO: 34:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (xi) SEQUENCE DESCRIPTION: SEQ ID NO: 34:

```
GGATATCACC CGATGTGCGG CGCTCCGCCG GNNTGTTTCC TATGATGAAT A TAGATACAG   60
AAGCG                                                                65
```

(2) INFORMATION FOR SEQ ID NO: 35:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO: 35:

```
GCCTGGCACC ATTAAAGAAA ATATCATCTT TGCCCACGAA AT                       42
```

(2) INFORMATION FOR SEQ ID NO: 36:

(i) SEQUENCE CHARACTERISTICS:
        (A) LENGTH: 96 base pairs
        (B) TYPE: nucleic acid
        (C) STRANDEDNESS: single
        (D) TOPOLOGY: linear (xi) SEQUENCE DESCRIPTION: SEQ ID NO: 36:

CCTTGTCTCC GTTCTGGATA TCACCCGATG TGTCTCCCTA TAGTGAGTCG T ATTAATTTC    60

NNGGTGTTTC CTATGATGAA TATAGATACA GAAGCG    96

(2) INFORMATION FOR SEQ ID NO: 37:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (xi) SEQUENCE DESCRIPTION: SEQ ID NO: 37:

GATGACGCTT CTGTATCTAT ATTCATCATA GGAAACACCT TAAAGATGAT A TTTTCTTTA    60

ATGGTGCCAG GCATAATCCA GG    82

(2) INFORMATION FOR SEQ ID NO: 38:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 38:

GATGACGCTT CTGTATCTAT ATTCATCATA GGAAACACCG ATGATATTTT C TTTAATGGT    60

GCCAGGCATA ATCCAGG    77

(2) INFORMATION FOR SEQ ID NO: 39:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO: 39:

GGGCTGACCC TCCCGGGGGC TGCGCCCACG AAAT    34

(2) INFORMATION FOR SEQ ID NO: 40:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (xi) SEQUENCE DESCRIPTION: SEQ ID NO: 40:

CCTTGTCTCC GTTCTGGATA TCACCCGATG TGTCTCCCTA TAGTGAGTCG T ATTAATTTC    60

NNACTCTCGT CCTGCTGGGA AGGGCGATAG T    91

(2) INFORMATION FOR SEQ ID NO: 41:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (xi) SEQUENCE DESCRIPTION: SEQ ID NO: 41:

TGAGTGCTCA GAGGAGGACT ATCGCCCTTC CCAGCAGGAC GAGTGCAGCC C CCGGGAGGG    60

TCAGCCCGTC TGCAGCCAGC GGGGCGAGTG CCTCT    95

(2) INFORMATION FOR SEQ ID NO: 42:

(i) SEQUENCE CHARACTERISTICS:
        (A) LENGTH: 95 base pairs
        (B) TYPE: nucleic acid
        (C) STRANDEDNESS: single
        (D) TOPOLOGY: linear (xi) SEQUENCE DESCRIPTION: SEQ ID NO: 42:

```
TGAGTGCTCA GAGGAGGACT ATCGCCCTTC CCAGCAGGAC GAATGCAGCC C CCGGGAGGG      60

TCAGCCCGTC TGCAGCCAGC GGGGCGAGTG CCTCT                                  95
```

(2) INFORMATION FOR SEQ ID NO: 43:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 43:

```
GATGACGCTT CTGTATCTAT ATTCATCATA GGAAACAAAG ATGATATTTT C TTTAATGGT      60

GCCAGGCATA ATCCAGG                                                      77
```

(2) INFORMATION FOR SEQ ID NO: 44:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (xi) SEQUENCE DESCRIPTION: SEQ ID NO: 44:

```
GATGACGCTT CTGTATCTAT ATTCATCATA GGAAACCAAA GATGATATTT T CTTTAATGG      60

TGCCAGGCAT AATCCAGG                                                     78
```

(2) INFORMATION FOR SEQ ID NO: 45:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (xi) SEQUENCE DESCRIPTION: SEQ ID NO: 45:

```
GATGACGCTT CTGTATCTAT ATTCATCATA GGAAAACAAA GATGATATTT T CTTTAATGG      60

TGCCAGGCAT AATCCAGG                                                     78
```

(2) INFORMATION FOR SEQ ID NO: 46:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO: 46:

```
GCCTGGCACC ATTAAAGAAA ATATCATCTT TGCCCACTTC GAAAT                       45
```

(2) INFORMATION FOR SEQ ID NO: 47:

(i) SEQUENCE CHARACTERISTICS:
        (A) LENGTH: 91 base pairs
        (B) TYPE: nucleic acid (C) STRANDEDNESS: single
        (D) TOPOLOGY: linear (xi) SEQUENCE DESCRIPTION: SEQ ID NO: 47:

GAATCTCATC AGTAGCGAGC TCTCTCTCCC TATAGTGAGT CGTATTAATT T CGAANNGGT    60

GTTTCCTATG ATGAATATAG ATACAGAAGC G    91

(2) INFORMATION FOR SEQ ID NO: 48:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 48:

GAAUCGAAAC GCGAAAGCGU CUAGCGU    27

(2) INFORMATION FOR SEQ ID NO: 49:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (xi) SEQUENCE DESCRIPTION: SEQ ID NO: 49:

TGCCTCCTTG TCTCCGTTCT GGATATCACC CGATGTGTCT CCCTATAGTG A GTCGTATTA    60

ATTTCAG    67

(2) INFORMATION FOR SEQ ID NO: 50:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO: 50:

GATGACGCTT CTGTATCTAT ATTCATCATA GGAAACACCA AGATATTTT C TTTAATGGT    60

GCCAGGCATA ATCCAGG    77

(2) INFORMATION FOR SEQ ID NO: 51:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (xi) SEQUENCE DESCRIPTION: SEQ ID NO: 51:

GATGACGCTT CTGTATCTAT ATTCATCATC GGAAACACCA AGATGATAT T TTCTTTAAT    60

GGTGCCAGGC ATAATCCAGG    80

(2) INFORMATION FOR SEQ ID NO: 52:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (xi) SEQUENCE DESCRIPTION: SEQ ID NO: 52:

GATGACGCTT CTGTATCTAT ATTCATCATA GGAAACACCA AGATGCTAT T TTCTTTAAT    60

-continued

```
GGTGCCAGGC ATAATCCAGG                                               80
```

(2) INFORMATION FOR SEQ ID NO: 53:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (xi) SEQUENCE DESCRIPTION: SEQ ID NO: 53:

```
GATGACGCTT CTGTATCTAT ATTCATCATC GGAAACACCA AAGATGCTAT T TTCTTTAAT    60

GGTGCCAGGC ATAATCCAGG                                               80
```